United States Patent
Johnson, Jr. et al.

(10) Patent No.: US 9,612,240 B2
(45) Date of Patent: Apr. 4, 2017

(54) BIOMIMETIC CHEMICAL SENSORS USING NANOELECTRONIC READOUT OF OLFACTORY RECEPTORS

(75) Inventors: Alan T. Johnson, Jr., Philadelphia, PA (US); Brett R. Goldsmith, Philadelphia, PA (US); Joseph J. Mitala, Jr., Rockville, MD (US); Bohdana Discher, Philadelphia, PA (US); Stephen G. Sligar, Urbana, IL (US); Timothy H. Bayburt, Champaign, IL (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 819 days.

(21) Appl. No.: 13/807,323

(22) PCT Filed: Jun. 29, 2011

(86) PCT No.: PCT/US2011/042290
§ 371 (c)(1),
(2), (4) Date: Aug. 14, 2013

(87) PCT Pub. No.: WO2012/050646
PCT Pub. Date: Apr. 19, 2012

(65) Prior Publication Data
US 2015/0065363 A1    Mar. 5, 2015

Related U.S. Application Data

(60) Provisional application No. 61/359,414, filed on Jun. 29, 2010.

(51) Int. Cl.
*G01N 33/543* (2006.01)
*G01N 33/554* (2006.01)

(52) U.S. Cl.
CPC ....... *G01N 33/5438* (2013.01); *G01N 33/554* (2013.01); *G01N 2333/726* (2013.01)

(58) Field of Classification Search
None
See application file for complete search history.

(56) References Cited

U.S. PATENT DOCUMENTS

| 5,369,028 | A | * | 11/1994 | Harpold | C12Q 1/6897 435/252.3 |
|---|---|---|---|---|---|
| 2003/0124572 | A1 | | 7/2003 | Umek et al. | |
| 2007/0292896 | A1 | | 12/2007 | Strano et al. | |
| 2008/0283875 | A1 | | 11/2008 | Mukasa | |
| 2009/0053212 | A1 | | 2/2009 | Yamamoto | |
| 2009/0084678 | A1 | | 4/2009 | Joshi | |
| 2009/0275066 | A1 | | 11/2009 | Popot et al. | |
| 2010/0270543 | A1 | | 10/2010 | Choi | |

FOREIGN PATENT DOCUMENTS

WO    WO 2010/014903 A1    2/2010

OTHER PUBLICATIONS

Nakanishi, S., Molecular Diversity of Glutamate Receptors and Implications for Brain Function, Oct. 23, 1992, Science 258:597-603.*
Zhang et al., Coding of Sweet, Bitter, and Umami Tastes: Different Receptor Cells Sharing Similar Signaling Pathways, Feb. 7, 2003, Cell 112:293-301.*
Suwa et al., OR2AG1—Olfactory receptor 2AG1—*Homo sapiens*, Jul. 2001, UniProtKB-Q9H205: 12 pages.*
Abaffy, T. et al., "Functional analysis of a mammalian odorant receptor subfamily", Journal of Neurochemistry 2006, 97, (5), 1506-1518.
Akimov, V., et al., "Nanobiosensors based on individual olfactory receptors", Analog Integrated Circuits and Signal Processing, 2008. 57(3): p. 197-203.
Albert, K.J., et al., "Cross-reactive chemical sensor arrays", Chemical Reviews, 2000. 100(7): p. 2595-2626.
Azpiazu, I. and N. Gautam, "A fluorescence resonance energy transfer-based sensor indicates that receptor access to a G protein is unrestricted in a living mammalian cell", Journal of Biological Chemistry, 2004. 279(26): p. 27709-27718.
Bahr, J.L., et al., "Functionalization of carbon nanotubes by electrochemical reduction of aryl diazonium salts: A bucky paper electrode", Journal of the American Chemical Society, 2001. 123(27): p. 6536-6542.
Bayburt, T. H. et al., "Self-assembly of discoidal phospholipid bilayer nanoparticles with membrane scaffold proteins", Nano Letters 2002, 2, (8), 853-856.
Bayburt, T.H. and S.G. Sligar, "Membrane protein assembly into Nanodiscs", Febs Letters, 2010. 584(9): p. 1721-1727.
Bayburt, T.H. and S.G. Sligar, "Self-assembly of single integral membrane proteins into soluble nanoscale phospholipid bilayers", Protein Science, 2003. 12(11): p. 2476-2481.
Bradley, K., et al., "Integration of cell membranes and nanotube transistors", Nano Letters, 2005. 5(5): p. 841-845.
Breer, H., "Olfactory receptors: molecular basis for recognition and discrimination of odors", Analytical and Bioanalytical Chemistry, 2003. 377(3): p. 427-433.
Chen, R. J. et al., "Noncovalent functionalization of carbon nanotubes for highly specific electronic biosensors", Proceedings of the National Academy of Sciences of the United States of America 2003, 100, (9), 4984-4989.
Christophe, C., et al., "Rats for demining: an overview of the APOPO program", Proceedings of the Eudem Conference on humanitarian landmine detection technologies, 2004, 5 pages.
Collins, P.G., et al., "Extreme oxygen sensitivity of electronic properties of carbon nanotubes", Science, 2000. 287(5459): p. 1801-1804.
D.J. Wasilko and S.E. Lee "TIPS: Titerless Infected-Cells Preservation and Scale-up" (2006), Bioprocessing Journal, vol. 5, No. 3. 29-32, Abstract only.

(Continued)

*Primary Examiner* — John Ulm
(74) *Attorney, Agent, or Firm* — Baker & Hostetler LLP

(57) ABSTRACT

The present invention provides biomimetic sensor devices that utilize proteins—such as G-protein coupled receptors—and are useful in high-sensitivity analysis of analyte-containing samples. These sensors may be used to determine the presence or concentration of one or more analytes in a sample. The invention also includes methods of fabricating the devices and methods of using the devices to assay samples.

22 Claims, 27 Drawing Sheets

(56) References Cited

OTHER PUBLICATIONS

Dan, Y.P., et al., "Intrinsic Response of Graphene Vapor Sensors", Nano Letters, 2009. 9(4): p. 1472-1475.
Denisov, I. G. et al., "Directed self-assembly of monodisperse phospholipid bilayer nanodiscs with controlled size", Journal of the American Chemical Society 2004, 126, (11), 3477-3487.
Duchamp-Viret, P. et al., "Odor response properties of rat olfactory receptor neurons", Science, 1999. 284(5423): p. 2171-2174.
Filmore, D., "It's a GPCR World", Modern Drug Discovery, 2004. 7(11): p. 24-28.
Furton, K.G. and L.J. Myers, "The scientific foundation and efficacy of the use of canines as chemical detectors for explosives", Talanta, 2001. 54(3): p. 487-500.
Goldsmith et al., "Biomimetic Chemical Sensors Using Nanoelectronic Readout of Olfactory Receptor Proteins", ACS Nano. Jun. 22, 2011, 5(7), pp. 5408-5416.
Goldsmith, B.R., et al., "Conductance-controlled point functionalization of single-walled carbon nanotubes", Science, 2007. 315(5808): p. 77-81.
Graff, R.A., et al., "Synthesis of nickel-nitrilotriacetic acid coupled single-walled carbon nanotubes for directed self-assembly with polyhistidine-tagged proteins", Chemistry of Materials, 2008. 20(5): p. 1824-1829.
Guo, X., et al., "Covalently bridging gaps in single-walled carbon nanotubes with conducting molecules", Science, 2006. 311: p. 356-9.
Heller, I., et al., "Identifying the mechanism of biosensing with carbon nanotube transistors", Nano Letters, 2008. 8(2): p. 591-595.
Kajiya, K. et al., "Molecular bases of odor discrimination: Reconstitution of olfactory receptors that recognize overlapping sets of odorants", Journal of Neuroscience 2001, 21, (16), 6018-6025.
Khafizov, K., et al., "Ligand specificity of odorant receptors" Journal of Molecular Modeling, 2007. 13(3): p. 401-409.
Khalap, V.R., et al., "Hydrogen Sensing and Sensitivity of Palladium-Decorated Single-Walled Carbon Nanotubes with Defects", Nano Letters, 2010. 10(3): p. 896-901.
Kim, T. H. et al., "Single-Carbon-Atomic-Resolution Detection of Odorant Molecules using a Human Olfactory Receptor-based Bioelectronic Nose", Advanced Materials 2009, 21, (1), 91-94.
Kojima, A., et al., "Protein sensor using carbon nanotube field effect transistor", Japanese Journal of Applied Physics Part 1—Regular Papers Short Notes & Review Papers, 2005. 44(4A): p. 1596-1598.
Kuang, Z.F., et al., "Biomimetic Chemosensor: Designing Peptide Recognition Elements for Surface Functionalization of Carbon Nanotube Field Effect Transistors", Acs Nano, 2010. 4(1): p. 452-458.
Lee, T.M.H., "Over-the-counter biosensors: Past, present, and future", Sensors, 2008. 8(9): p. 5535-5559.
Lu, Y. et al., "DNA-decorated graphene chemical sensors", Applied Physics Letters 2010, 97, (8), 083107.
McAlpine, M.C., et al., "Peptide-nanowire hybrid materials for selective sensing of small molecules", Journal of the American Chemical Society, 2008. 130(29): p. 9583-9589.
Misra et al., "Bioelectronic silicon nanowire devices using functional membrane proteins", PNAS, Aug. 18, 2009, 106(33), 13780-13784.
Noy, A. et al., "Bionanoelectronics with 1D materials", Materials Today, 2009. 12(9): p. 22-31.
Peng, X.H. et al., "Functional Covalent Chemistry of Carbon Nanotube Surfaces", Advanced Materials, 2009, 21(6), 625-642.
Pengfei, Q.F., et al., "Toward large arrays of multiplex functionalized carbon nanotube sensors for highly sensitive and selective molecular detection", Nano Letters, 2003. 3(3): p. 347-351.
Pevsner, J. et al., "Isolation and Characterization of an Olfactory Receptor Protein for Odorant Pyrazines", Proceedings of the National Academy of Sciences of the United States of America 1985, 82, (9), 3050-3054.
Raming, K., et al., "Cloning and Expression of Odorant Receptors", Nature, 1993. 361(6410): p. 353-356.
Repicky, S.E. and C.W. Luetje, "Molecular receptive range variation among mouse odorant receptors for aliphatic carboxylic acids", Journal of Neurochemistry, 2009. 109(1): p. 193-202.
Ritchie, T. K. et al., "Reconstitution of Membrane Proteins in Phospholipid Bilayer Nanodiscs", Methods in Enzymology; Liposomes, Pt F 2009, 464, 211-231.
Saito, H. et al., "Odor Coding by a Mammalian Receptor Repertoire", Science Signaling, Nov. 2009, 2, (60), ra9.
Schwende, F.J. et al., "Volatile Compounds Associated with Estrus in Mouse Urine—Potential Pheromones", Experientia, 1984. 40(2): p. 213-214.
Staii, C. and A.T. Johnson, "DNA-decorated carbon nanotubes for chemical sensing", Nano Letters, 2005. 5(9): p. 1774-1778.
Star, A., et al., "Electronic detection of specific protein binding using nanotube FET devices", Nano Letters, 2003. 3(4): p. 459-463.
Sun, S.J., "Gas adsorption on a single walled carbon nanotube-model simulation", Physics Letters A, 2008. 372(19): p. 3493-3495.
Tang, X. et al., "Carbon Nanotube DNA Sensor and Sensing Mechanism", Nano Letters 2006, 6, (8), 1632-1636.
Uchida, N. and Z.F. Mainen, "Speed and accuracy of olfactory discrimination in the rat", Nature Neuroscience, 2003. 6(11): p. 1224-1229.
Wasilko, D. J. et al., "The titerless infected-cells preservation and scale-up (TIPS) method for large-scale production of NO-sensitive human soluble guanylate cyclase (sGC) from insect cells infected with recombinant baculovirus", Protein Expression and Purification 2009, 65, (2), 122-132.
White, J., et al., "Solid-state, dye-labeled DNA detects volatile compounds in the vapor phase", Plos Biology, 2008. 6(1): p. 30-36.
Wilson, D.A., "Habituation of odor responses in the rat anterior piriform cortex", Journal of Neurophysiology, 1998. 79(3): p. 1425-1440.
Wise, P.M. et al., "Quantification of odor quality", Chemical Senses, 2000. 25(4): p. 429-443.
Xu, F.Q., et al., "Simultaneous activation of mouse main and accessory olfactory bulbs by odors or pheromones", Journal of Comparative Neurology, 2005. 489(4): p. 491-500.
Yoon, H., et al., "Polypyrrole Nanotubes Conjugated with Human Olfactory Receptors: High-Performance Transducers for FET-Type Bioelectronic Noses", Angewandte Chemie-International Edition, 2009. 48(15): p. 2755-2758.
Zhang, X. M. et al., "High-throughput microarray detection of olfactory receptor gene expression in the mouse", Proceedings of the National Academy of Sciences of the United States of America 2004, 101, (39), 14168-14173.
Zhang, Y.B., et al., "Functionalized carbon nanotubes for detecting viral proteins", Nano Letters, 2007. 7(10): p. 3086-3091.
Zhou, X.J., et al., "Supported lipid bilayer/carbon nanotube hybrids", Nature Nanotechnology, 2007. 2(3): p. 185-190.
Zuniga, C., et al., "Nanoenabled microelectromechanical sensor for volatile organic chemical detection", Applied Physics Letters, 2009. 94(22): p. 223122.

* cited by examiner

FIG. 9

|  | mOR174-9 | mOR203-1 | mOR256-17 |
|---|---|---|---|
| Eugenol | X X | O O | X O |
| 2-heptanone | O O | X X | X X |
| Heptanal | O O | O O | O X |
| Acetophenone | O O | O O | O X |
| Cyclohexanone | X O | O O | X X |
| 2,4-DNT | O O | X X | X X |
| Amyl acetate | O O | Not tested | O O |
| Methyl benzoate | O O | Not tested | O O |

Legend: An "X" indicates a strong response at a relevant concentration.
An "O" indicates little to no response at a relevant concentration.

For each table entry, the first (left) box represents the result from the inventive OR-functionalized nanotube sensor, the second (right) box represents the result from the Xenopus oocyte (frog egg).

Accordingly, two "X" or two "O" boxes indicates that the inventive sensors and the Xenopus oocyte agreed (i.e., had similar responses) for a particular OR/analyte combination.

An entry with an "X" and an "O" box indicates that the methods disagree for the given combination of OR and analyte.

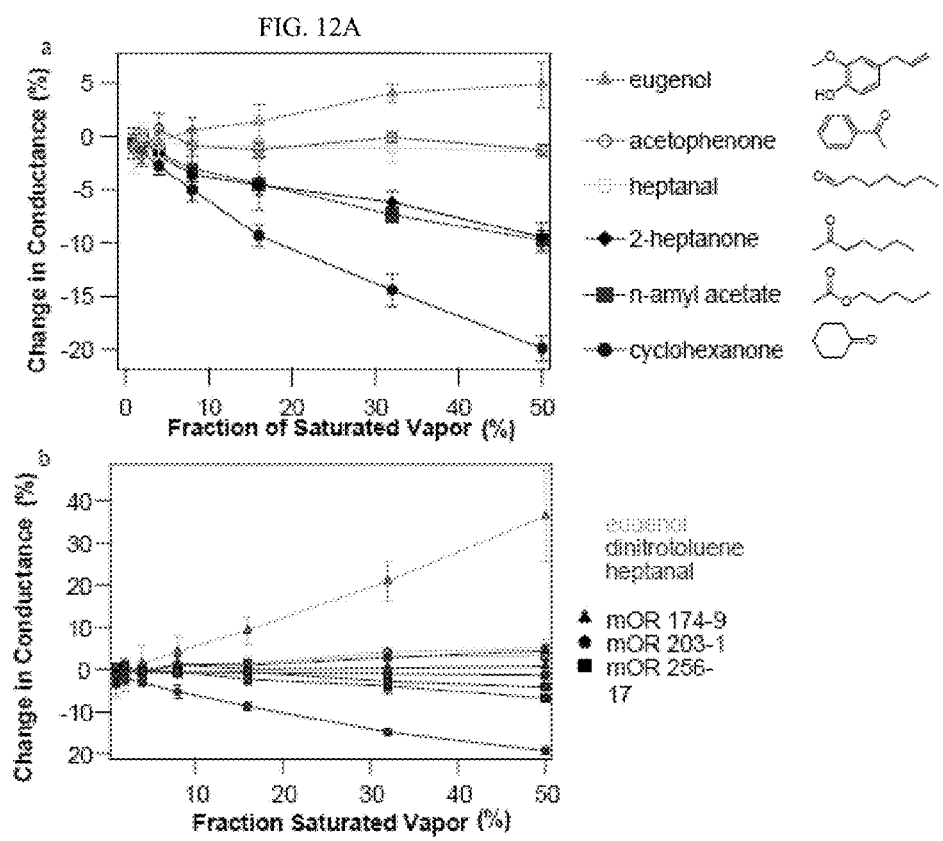

FIG. 13

| | mOR 174-9 | | | mOR 203-1 | | | mOR 256-17 | | | no OR | |
|---|---|---|---|---|---|---|---|---|---|---|---|
| | Xenopus oocyte | micelle nanotube | nanodisc nanotube | HEK | micelle nanotube | nanodisc nanotube | Xenopus oocyte | micelle nanotube | nanodisc nanotube | empty micelle | bare NT |
| eugenol | -8.4 | +20.9±4.6 | +7.2±1.1 | 0 | +4.0\±0.8 | +2.3±1.7 | 0 | +3.0±0.8 | +33.6±8.3 | +0.5±1.3 | 0.0±0.2 |
| 2-heptanone | 0 | +4.1±2.2 | -3.3±3.4 | -4.76 | -6.2±1.1 | -6.5±1.5 | -9.57 | -10.5±0.8 | -2.1±0.6 | -0.7±0.5 | +0.6±1.2 |
| heptanal | 0 | +2.8±1.1 | +5.4±3.1 | 0 | -1.1±1.4 | -2.2±0.9 | -5.30 | -3.9±2.0 | -0.7±0.6 | +1.7±1.7 | +0.2±0.6 |
| acetophenone | 0 | +6.1±0.8 | -4.2±1.0 | 0 | -0.1±0.5 | -9.6±0.7 | -5.93 | +0.2±0.7 | -2.3±0.8 | +1.3±1.2 | -0.1±0.1 |
| 2,4 DNT | 0 | +0.2±2.0 | -7.7±1.2 | | -15.0±0.6 | -0.7±2.0 | -4.67 | -2.9±2.7 | -23.0±3.1 | +0.1±0.7 | +0.1±0.1 |
| n-amyl acetate | 0 | 0 | -4.4±0.4 | | -7.4±0.7 | -11.0±1.2 | 0 | -16.5±1.0 | -3.2±0.5 | +0.9±1.4 | +0.5±0.6 |
| methyl benzoate | 0 | +5.6±1.9 | -4.2±0.9 | | -0.9±1.9 | -1.6±1.8 | 0 | -3.9±0.8 | +2.7±3.4 | +0.3±0.6 | +0.3±0.7 |
| cyclohexanone | 0 | -28.2±1.6 | -14.9±0.6 | 0 | -14.4±1.5 | -10.5±0.4 | -1.00 | -29.2±1.6 | -35.3±3.9 | +1.8±3.7 | 0.0±0.2 |

FIG. 22C
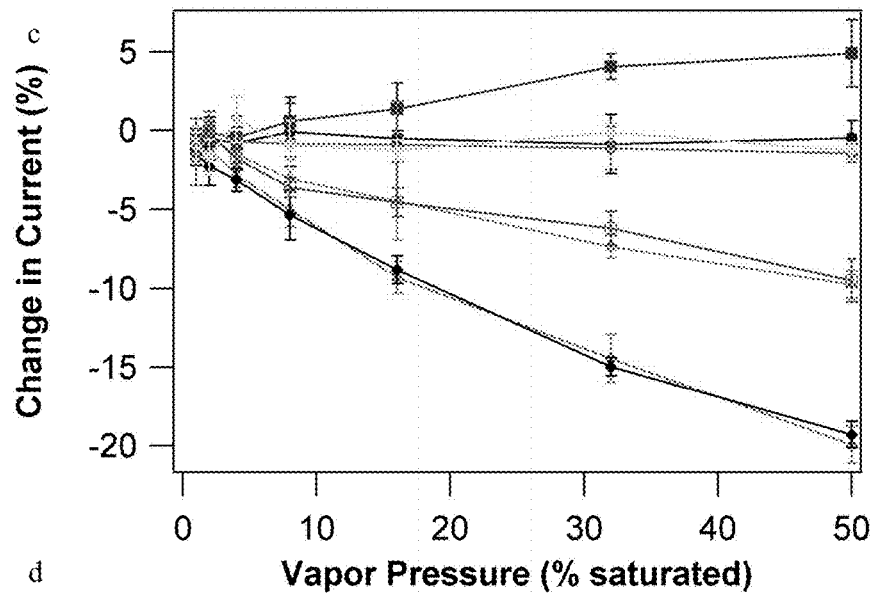
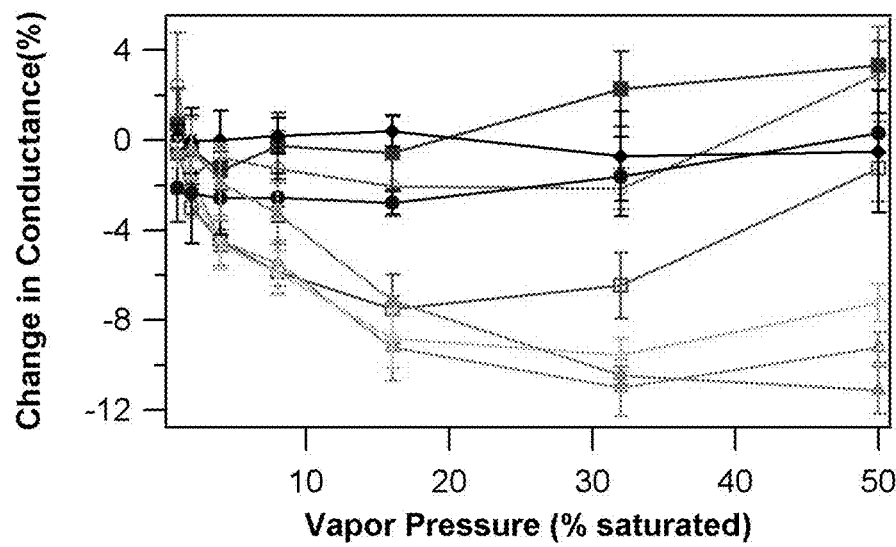
FIG. 22D

BIOMIMETIC CHEMICAL SENSORS USING NANOELECTRONIC READOUT OF OLFACTORY RECEPTORS

RELATED APPLICATIONS

This application is the National Stage of International Application No. PCT/US2011/042290, filed Jun. 29, 2011, which application claims the benefit of U.S. Provisional Application No. 61/359,414, filed Jun. 29, 2010. The foregoing applications are incorporated herein by reference in their entireties for any and all purposes.

STATEMENT OF GOVERNMENT RIGHTS

This invention was made with government support under HR0011-09-C-0013, Amend 2, awarded by the Defense Advanced Research Products Agency (DARPA), NSEC DMR08-32802, awarded by the National Science Foundation, and PCRP #PC080542P1, awarded by the Department of Defense. The government has certain rights in this invention.

SEQUENCE LISTING

The instant application contains a Sequence Listing which has been submitted in ASCII format via EFS-Web and is hereby incorporated by reference in its entirety. Said ASCII copy, created on Jan. 28, 2013, is named Sequence_Listing_CRF_UPN5806 and is 1,147 bytes in size.

TECHNICAL FIELD

The present invention relates to the fields of biomimetic sensors and sensor devices. The present invention also relates to the field of membrane proteins.

BACKGROUND

Integration of modern nanoelectronic technology with the potent molecular machines of living organisms offers a pathway to advanced modalities for chemical sensing, high throughput screening of ligand binding, and other applications. Despite their vital roles in living systems, and the impressive range of functionalities that they exhibit (including energy harvesting and ultrasensitive chemical detection), there has been little progress in the field of nanoelectronic integration of membrane proteins and other amphiphilic species.

Efforts in this direction have encountered a number of difficulties associated with the hydrophobic nature of the transmembrane domains of membrane proteins, which complicates the proteins' expression, purification, solubilization, and integration with nanoelectronic systems, particularly in an ambient environment. Accordingly, there is a need in the art for devices that take advantage of the sensitivity of membrane proteins. There is also a need in the art for related methods of fabricating and using such devices.

SUMMARY

In meeting the described challenges, the present invention first provides devices, the devices comprising a semiconductor material; and a transmembrane protein, the protein capable of changing conformation upon binding to a target, the transmembrane protein disposed in a support material capable of maintaining the protein in essentially its natural conformation, and the transmembrane protein being in electrical communication with the semiconductor material.

The invention also provides methods of assembling a sensor. These methods include placing a transmembrane protein disposed in a lipid, an amphiphile, or both, into electronic communication with a semiconductor material.

Further provided are methods of assaying a sample, comprising contacting a sample with a device comprising a transmembrane protein disposed in a lipid, an amphiphile, or both, the device comprising a semiconductor material in electronic communication with the transmembrane protein; and measuring a first electronic characteristic of the device when the device is contacted with the sample.

Additionally provided are sensor systems, comprising a protein in essentially its natural conformation, the protein being in electronic communication with a semiconductor material; and a detector device capable of detecting changes in one or more electronic characteristics of the protein related to an interaction between the protein and an analyte.

Integrating mammalian olfactory proteins in an electronic chemical sensor designed to work in ambient air is a major step forward in the integration of molecular biology and nanoelectronics. For the first time, a path is available for the creation of an electronic nose that can be directly compared to biological noses.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings:

—FIG. 3A illustrates the sensing response to cyclohexanone at 2250 ppm, where individual points are raw data, and the solid line is a double exponential fit with time constants of 9.1 s and 41.2 s. Introduction of cyclohexanone starts at 0 seconds, and FIG. 3B illustrates sensor recovery after the response shown here (flushing of the chamber with nitrogen starts at 0 seconds), the recovery can be fit with a single exponential with a time constant of 25.3 s;

FIG. 9 illustrates the agreement between ORs disposed in the inventive, synthetic devices and ORs disposed in a living carrier.

FIG. 10A provides a schematic of a carbon nanotube transistor functionalized with mORs in nanodiscs, FIG. 10B provides AFM image demonstrating preferential attachment of His-tag labeled mOR 174-9 (dark circles) in micelles to Ni-NTA functionalized carbon nanotubes (lines). There is a preference for attachment to the functionalized nanotubes compared to the background, FIG. 10C is $I(V_G)$ curves of the same nanotube device as-fabricated (red squares), after Ni-NTA functionalization (green circles) and after incubation in a solution of mORs in digitonin micelles (black diamonds). The change in $I(V_G)$ associated with Ni-NTA functionalization is consistent with expectations based on association of $Ni^{+2}$ atoms with NTA attached to the nanotube. The change in $I(V_G)$ seen after mOR attachment is typical for protein-functionalization of nanotube devices. Data collected with a bias voltage of 100 mV FIG. 11A provides three sets of responses to 2 ppm eugenol vapor taken over multiple days using a nanotube transistor functionalized with mOR174-9 in digitonin micelles. Eugenol vapor is introduced at time 0, and every 200 seconds (solid vertical lines). The chamber is flushed each time after 100 seconds of exposure (dashed vertical lines). Although the device baseline current shows significant drift over five days, the normalized current changes are identical, as seen in FIG. 11B. FIG. 11C illustrates a characterization of nanodisc packaged OR-NT devices over 10 weeks. The device is based on mOR174-9 in nanodiscs, exposed to 2 ppm eugenol as described in FIG. 11A, and FIG. 11D illustrates response to 2250 ppm cyclohexanone and recovery for a nanotube device functionalized with mOR 256-17 in nanodiscs, with 200 µs resolution. Flow of cyclohexanone begins at time=0 s and flow is replaced with clean $N_2$ at time=100 s. Individual points are raw data, and the line represents a line fit based on double exponential functions. Response time constants are 2.06±0.01 and 25.51±0.04 sec. Recovery time constants are 6.49±0.04 and 38.0±0.2 sec (error bars are statistical based on the data in the figure). NT device time scales are more rapid than those observed in heterologous expression systems (~5-10 minutes), which rely on a cellular signal transduction pathway to report receptor activation.

FIGS. 12A-12B illustrate the dependence of device responses upon mOR identity, odorant identity, and odorant concentration. FIG. 12A Concentration dependence of responses of NT devices functionalized with mOR203-1 in digitonin micelles to vapors of six different odorants. FIG. 12B provides a concentration dependence of the responses for NT devices functionalized with different mORs, tested against eugenol, 2,4-dinitrotoluene and heptanal. The data demonstrate the diversity of chemical and concentration dependent responses seen in the mOR-NT system. Error bars are standard deviation.

FIG. 13 summarizes (in table form, Table I) the responses of mouse olfactory receptor proteins (mORs) to selected odorants, in biological and electronic systems;

FIG. 20B illustrates digitonin micelles containing His-tagged proteins also selectively bind to Ni-NTA functionalized carbon nanotubes. 30 nm height color scale. FIG. 20C illustrates that digitonin micelles do not preferentially bind to un-functionalized carbon nanotubes. 30 nm height color scale.

FIGS. 22A-22F present data summarizing responses across all functionalized device types, all odorants, and all concentrations used in the experiments. FIG. 22A provides data for mOR 174-9 in digitonin micelles. FIG. 22B provides data for mOR 174-9 in nanodiscs. FIG. 22C provides data for mOR 203-1 in digitonin micelles. FIG. 22D provides data for mOR 203-1 in nanodiscs. FIG. 22E provides data for mOR 256-17 in digitonin micelles. FIG. 22F provides data for mOR 256-17 in nanodiscs;

DETAILED DESCRIPTION OF ILLUSTRATIVE EMBODIMENTS

Figures 1A, 1B, 1C:
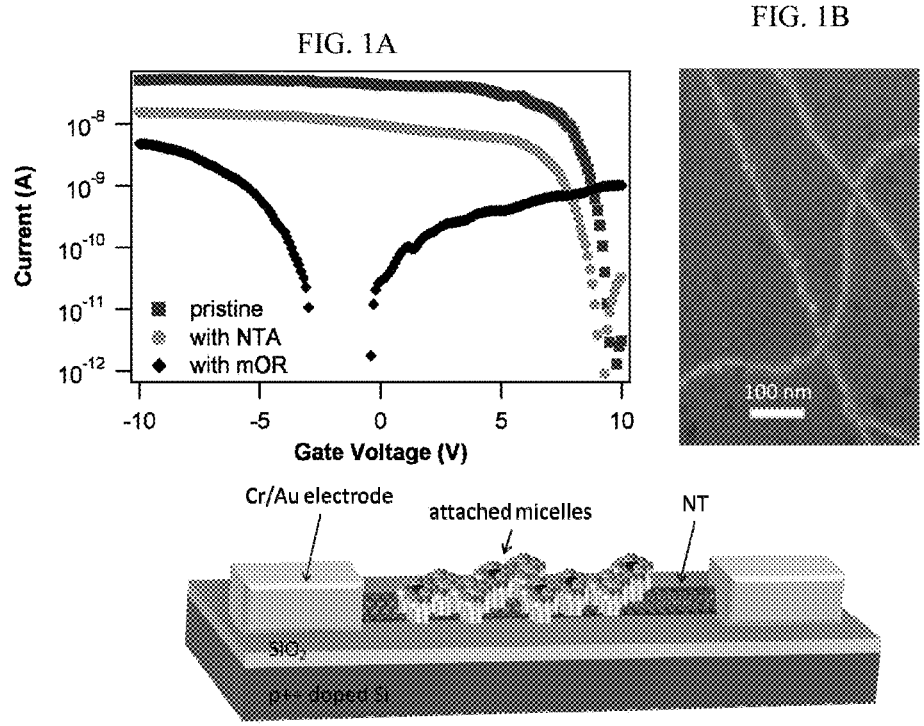
FIG. 1A I(Vg) traces of a carbon nanotube device in its pristine state (squares), after diazonium-NTA-Ni functionalization (circles) and after mOR incubation (diamonds) in digitonin micelles—a 100 mV bias across the nanotube is used in each curve.
FIG. 1B illustrates a SEM image demonstrating attachment of His-tag labeled 30 nm gold nanoparticles to carbon nanotubes using diazonium-NTA-His chemistry, and (FIG. 1C) a diagram of a carbon nanotube transistor functionalized with micelle solubilized ORs.

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range. Any and all documents cited in this application are incorporated herein by reference in their entireties.

As previously discussed, G-protein coupled receptors (GPCRs) are a large family of membrane proteins that sense molecules outside of cells and ultimately initiate cellular responses. GPCRs are involved in many human diseases and are the targets of approximately 50% of all modern medicinal drugs. Olfactory receptors (ORs) are the most numerous GPCRs, representing approximately 3% of the mammalian genome. They enable the remarkable efficiency of the mammalian olfactory system, which is capable of the identification and classification of thousands of odorant compounds with very low thresholds, even odorants that have not been encountered before. Despite significant technological development, the mammalian olfactory system remains the "gold standard" for portable chemical and explosives detection based on its superior sensitivity, accuracy and versatility in comparison to manmade systems. Integration of ORs with carbon nanotube transistors is of particular interest since they are known to exhibit very high sensitivity and are compatible with dense arraying as required in electronic nose applications. Additionally, the response characteristics of carbon nanotube based vapor sensors can be controlled through the use of chemical functionalization.

Described herein is the successful integration of exemplary protein receptors (GPCRs are used to illustrate the claimed invention) with read out electronics based on carbon nanotube (NT) transistors and transistors of other materials.

The olfactory receptors may be solubilized via using detergent micelles of digitonin. The receptors may also be solubilized using stable, water-soluble, self-assembling nanoscale membrane assemblies known as "nanodiscs." Other detergents/surfactants may be used to solubilize the proteins, and digitonin is considered particularly suitable. As the user of ordinary skill will readily appreciate, surfactants/detergents that enable the transmembrane protein of interest to maintain its natural conformation are especially suitable.

In a first aspect, the present invention provides devices. These devices are particularly suitable as sensors, and include a semiconductor material and a transmembrane protein capable of changing conformation upon binding to a target. The transmembrane protein is suitably disposed in a support material capable of maintaining the protein in essentially its natural conformation, and the protein is suitably in electrical communication with the semiconductor material. A variety of exemplary proteins are disclosed elsewhere herein.

The protein is suitably maintained in a conformation that is identical or close to identical to the protein's natural conformation. For example, this means that a GPCR is present—until it interacts with an analyte to which the GPCR is complementary—in its natural conformation or suitably at least in conformation that enables the GPCR to interact with that analyte. In some embodiments, the protein itself changes conformation upon interaction with a complementary analyte; it is this change in conformation that results in a change in an electronic property of the device (e.g., conductivity) that may then be detected and, in some embodiments, correlated to the presence of an analyte.

The semiconductor material is suitably a carbon nanotube, graphene, silicon carbide, or any combination thereof. Carbon nanotubes are considered especially suitable, as they are readily available and possess suitable semiconducting characteristics. Carbon nanotubes are also efficiently functionalized so as to enable attachment or linkage to a protein sensor (e.g., GPCR). Both single- and multi-wall carbon nanotubes are suitable for use in the inventive devices. Other semiconducting materials, such as oxides, doped silicon, and the like.

In some embodiments, a surface of the semiconductor material comprises a functional group linking the semiconductor to the transmembrane protein. In one non-limiting example, the surface of the material (e.g., a carbon nanotube) may be functionalized with functionalized with carboxylated diazonium salts, which spontaneously form covalent bonds to carbon nanotubes. Amine and amide functionalities are considered suitable, as are phenolic/aromatic functionalities. The nanotubes may include polymer chains linked to their surfaces. Metals, such as nickel, may also be included in—or coordinated with—the surface functionality of the semiconducting material. Biotin/avidin may also be used as functional species on the semiconductor material.

The material in which the proteins are suitably disposed suitably includes lipids, amphiphiles, or both. It is to be understood that the term "amphiphile" includes surfactants. Lipid membranes are considered suitable, including lipid membranes disposed in so-called nanodiscs. The surfactant may be ionic or nonionic, depending on the needs of the user. Micelles, such as those made from digitonin, are also suitable. The user of ordinary skill in the art will encounter little difficulty in determining the suitable lipid/amphiphile for use with a particular protein.

A variety of transmembrane proteins are suitable for the inventive devices. G-proteins and G-protein coupled receptors are considered especially suitable. As described elsewhere herein, such G-protein coupled receptors (GPCRs) are exquisitely sensitive to multiple analytes, and the use of GPCRs in the inventive devices enables the user to analyze a sample for the presence of multiple, diverse analytes. The GPCR may include an olfactory receptor (as described elsewhere herein). GPCRs generally include receptors for sensory signal mediators (e.g., light and olfactory stimulatory molecules).

Suitable GPCRs also include adenosine, bombesin, bradykinin, endothelin, γ-aminobutyric acid (GABA), hepatocyte growth factor (HGF), melanocortins, neuropeptide Y, opioid peptides, opsins, somatostatin, tachykinins, members of the vasoactive intestinal peptide family, and vasopressin; biogenic amines (e.g., dopamine, epinephrine, norepinephrine, histamine, glutamate (metabotropic effect), glucagon, acetylcholine (muscarinic effect), and serotonin); chemokines; lipid mediators of inflammation (e.g., prostaglandins, prostanoids, platelet-activating factor, and leukotrienes); and peptide hormones (e.g., calcitonin, C5a anaphylatoxin, follicle-stimulating hormone (FSH), gonadotropin-releasing hormone (GnRH), neurokinin, thyrotropin-releasing hormone (TRH), and oxytocin). The number of GPCRs and range of analytes detectable by such GPCRs make them especially suitable proteins for use in the present invention.

The devices suitably place the protein (e.g., GPCR) in electronic communication with the semiconducting material. One way to facilitate such communication is to link the protein to the surface of the semiconducting material. In one embodiment, the protein includes a histidine or other tag; tags suitably include peptide sequences genetically grafted onto a recombinant protein. Often these tags are removable by chemical agents or by enzymatic means, such as proteolysis or intein splicing. Tags are attached to proteins for various purposes. The user of ordinary skill will be familiar with the various tags that may be included with a protein. Suitable tags provide a point for linkage between the protein and the semiconductor. As one non-limiting example, a protein bearing a histidine tag may link or coordinate with nickel-nitrilotriacetic acid (Ni-NTA) present on a carbon nanotube. In some embodiments, the protein may be ionically or covalently bound to the semiconductor material. The tag may also be a biotin/avidin moiety, DNA, RNA, and the like.

Figure 14:
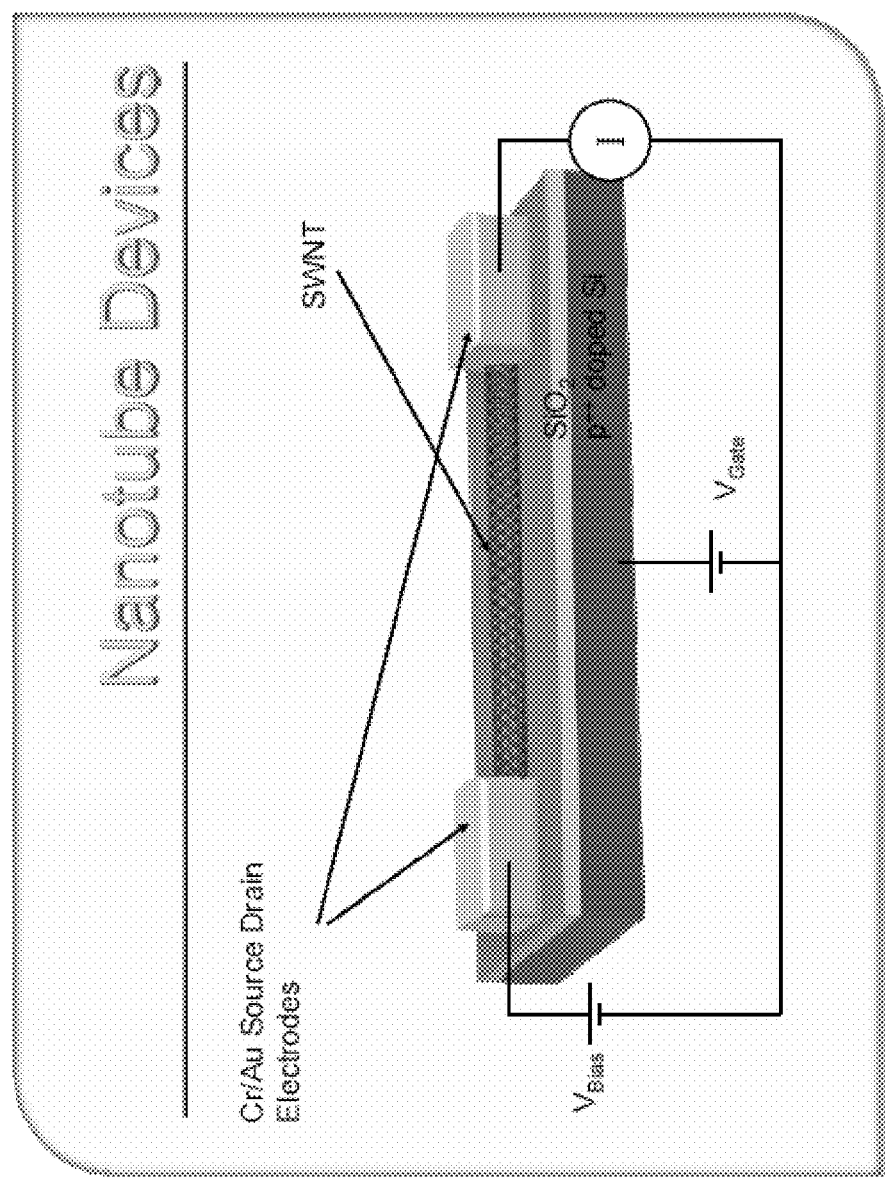
FIG. 14 depicts an exemplary device according to the present disclosure.

One exemplary device is shown in FIG. 1. That device includes a nanotube bound to GPCRs (not shown) that are disposed within amphiphile-made micelles, which micelles maintain the GPCRs in their natural conformation. The proteins are, as described above, linked to the nanotube, which linkage may be accomplished by a nickel-histidine interaction. The nanotube is suitably disposed between electrodes. A variety of substrates may be used in these devices; FIG. 1 shows substrate layers of SiO2 and p++ doped silicon. FIG. 14 depicts another illustrative device.

Sensor systems may also be constructed according to the present invention. These systems suitably include a protein in its natural conformation, the protein being in electronic communication with a semiconductor material; and a detector device capable of detecting changes in one or more electronic characteristics of the protein related to an interaction between the protein and an analyte.

The protein is suitably a membrane protein. G-proteins and GPCRs are considered especially suitable. As described elsewhere herein, the protein(s) are suitably disposed in a lipid, an amphiphile/surfactant, or both, so as to be maintained in essentially its natural conformation. The lipids and amphiphiles may be in layer or membrane form, and may also be in the form of micelles. Nanodiscs—also described herein—are suitable support materials.

Electronic communication between the protein and the semiconductor material may be effected by coordination, a covalent bond, an ionic bond, and the like. In one non-limiting embodiment, a histidine tag coordinates with nickel metal that is linked to a semiconductor substrate. Biotin-avidin, DNA-DNA, RNA-RNA, and other methods of linking the proteins to the substrates will be known to those in the art.

Semiconductors are suitably carbon nanotubes, graphene, silicon carbide, and the like. Nanotubes are considered especially suitable for systems and devices according to the present invention; as described elsewhere herein, nanotubes are readily available, and techniques for modifying the nanotubes' surfaces are known in the art.

A variety of devices may be used to detect changes in the electronic characteristic of the protein. Current monitors (e.g., Keithley 6485(TM)) is considered especially suitable. A computer may be used to control application of current and to monitor the electronic characteristics of the device in response to exposure to analytes.

The invention also provides methods of assembling sensors. These methods include placing a transmembrane protein disposed in a nanodisc or a lipid, an amphiphile, or both, into electronic communication with a semiconductor material.

As described elsewhere herein, the lipid, the amphiphile, or both, is selected so as to maintain the protein in essentially its natural configuration. A variety of proteins—including G-proteins and GPCRs—are suitable for the assembly process; the claimed invention enables the use of virtually any protein (including transmembrane proteins) or other sensor molecule that may normally resides in a lipid or amphiphile. The claimed invention thus allows the user to avail themselves of the functionality of transmembrane proteins.

The user may functionalize the semiconductor material so as to promote linkage between the protein and the semiconductor material. This may be done according to the methods of Graff, et al. (2008). The user suitably links the semiconductor material to the transmembrane protein. This may be effected by a histidine-nickel interaction, wherein the histidine resides as a "tag" on the protein. The user suitably places tags and functionalities on the protein and semiconductor material so as to effect a robust linkage between the two that places the two items in electronic communication with one another. Functionalization of the semiconductor surface enables controllable, rapid assembly of the inventive devices.

In some non-limiting, tested embodiments, solubilized olfactory receptors (ORs) were attached via a polyhistidine tag (His-tag) to nanotube transistors that were functionalized with nickel-nitrilotriacetic acid (Ni-NTA). These OR-NT devices exhibited responses to gaseous odorants that do not cause a detectable conductivity change in bare NT devices, as shown in FIG. 1. The electrical responses were reproducible for both single devices and between devices, as well as rapid and reversible (response and recovery time on the order of seconds). The sign and magnitude of the electrical response was OR specific and a function of the odorant tested.

For the three different ORs that were integrated with NT transistor read out circuitry, measured electrical responses were in qualitative agreement with binding experiments conducted with biological surrogates. This performance is illustrated by FIG. 9, which presents this "agreement" data in tabular form.

In that figure, the results for mORs integrated into nanotubes devices are compared with the results for mORs in biological carriers/surrogates. For example, the box corresponding to the response of mOR174-9 to exposure to eugenol shows "X X", which indicates that at the relevant concentration of eugenol, an mOR integrated into a synthetic device (represented by the left-hand "X") exhibited a similar, strong response to the eugenol as an mOR integrated into a biological surrogate (represented by the right-hand "X"). Similarly, the box corresponding to mOR174-9 exposure to heptanal shows "O O", which indicates that at the relevant concentration of eugenol, an mOR integrated into a synthetic device (represented by the left-hand "O") exhibited a little to no response to eugenol, which was similar to the response to the eugenol from an mOR integrated into a biological surrogate (represented by the right-hand "O").

Entries on FIG. 9 that show an "X" and an "O" indicate that mORs integrated into nanotubes devices and mORs in biological carriers/surrogates exhibited different responses (or "disagreed") for a given combination of OR and analyte. For example, the box corresponding to the response of mOR174-9 to exposure to cyclohexanone shows "X O", which indicates that at the relevant concentration of cyclohexanone, an mOR integrated into a synthetic device (left-hand "X") exhibited a strong response to the cyclohexanone, while a mOR integrated into a biological surrogate (right-hand "O") exhibited little to no response to that analyte. As shown by this non-limiting tabulation, ORs integrated into the inventive devices and ORs present in biological surrogates generally "agreed" for most combinations of OR and analyte, thus underscoring that the inventive devices have harnessed the naturally-occurring sensitivity and performance of the receptors integrated into the devices.

To test whether the NTs can selectively and specifically detect odorant binding by olfactory receptors, inventive devices were tested against the eight odorants listed in Table 1. Mouse olfactory receptors (mORs) that bind these odorants were identified using a *Xenopus* oocyte expression system in combination with robotic electrophysiology, building on a significant literature describing the use of biological surrogates for determining mOR responses. Of the sixteen deorphanized mORs, three were selected for overexpression and integration with NT transistors for vapor response testing. Qualitative electrophysiology responses of the selected ORs when expressed in *Xenopus* oocytes is shown in Table 1 (below), which tabulates the electrophysiology responses of mouse olfactory receptors to selected odorants when expressed in *Xenopus* oocytes. "X" indicates a clear sensitivity, "nt" indicates not tested:

|               | mOR174-9 | mOR203-1 | mOR256-17 |
|---------------|----------|----------|-----------|
| Eugenol       | X        |          |           |
| 2-heptanone   |          | X        | X         |
| Heptanal      |          |          | X         |
| acetophenone  |          |          | X         |
| cyclohexanone |          |          | X         |
| 2,4-dinitrotoluene |     | nt       | X         |
| n-amyl acetate |         | nt       |           |
| methyl benzoate |        | nt       |           |

Recombinant mORs were expressed in Sf9 insect cells with an N-terminal His-tag to simplify the purification and guide the attachment to carbon nanotube devices. After harvesting the cells, target mORs were purified using a Ni-NTA resin.

Figure 16:
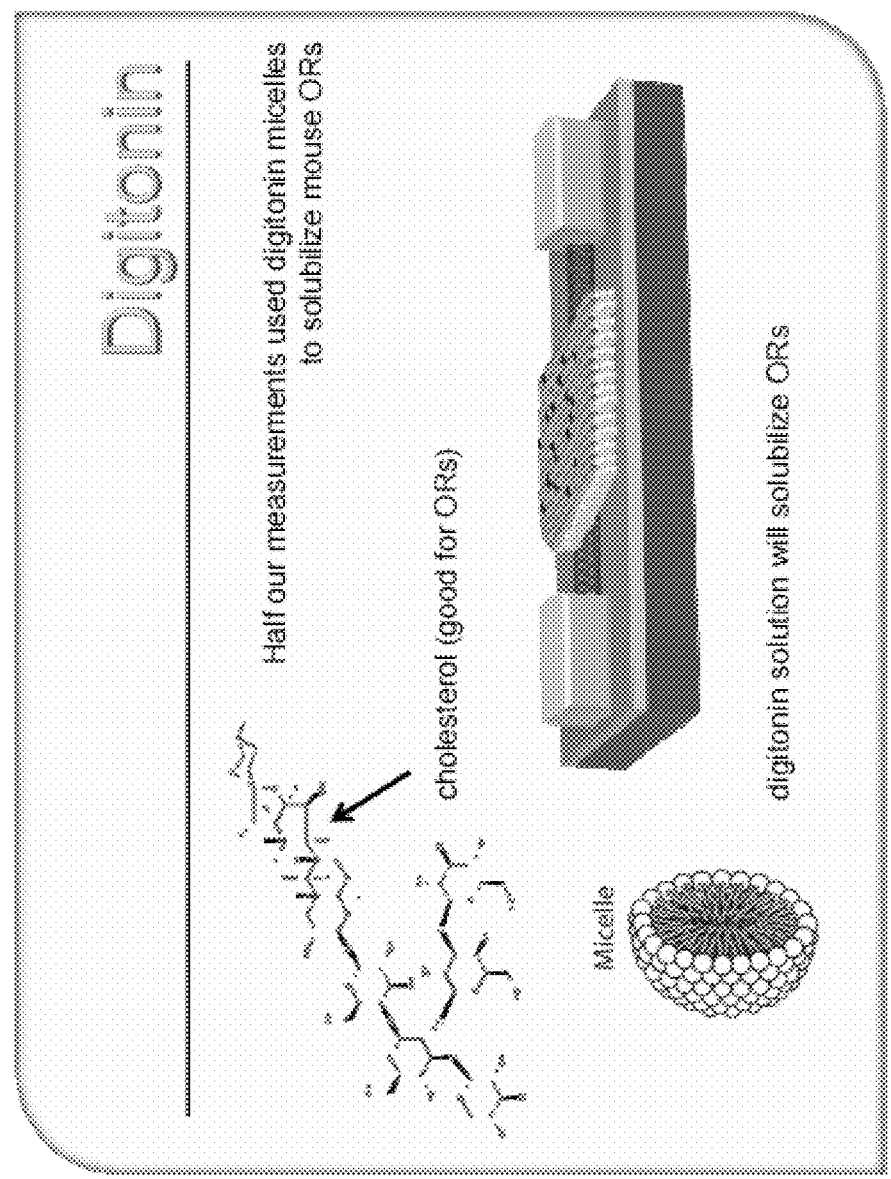
FIG. 16 depicts an exemplary embodiment of the present disclosure using digitonin as a stabilizer.

Throughout the purification process, the protein was maintained in approximately 4.88 mM (0.6% w/v) digitonin, a surfactant containing a cholesterol backbone that promotes functional solubilization of membrane proteins. Digitonin forms micelles at a concentration above about 0.5 mM, which micelles serve as temporary surrogate cell membranes, in which individual membrane proteins are embedded. Other amphiphiles beside digitonin may be used; the user of ordinary skill in the art will readily determine which amphiphile(s) are suited to particular proteins. At this point, the mORs were attached to the nanotube transistors, yielding functional vapor sensors. An exemplary device is shown in FIG. 16, which figure illustrates an assembled device with ORs stabilized by digitonin on a nanotube transistor device.

Figure 17:
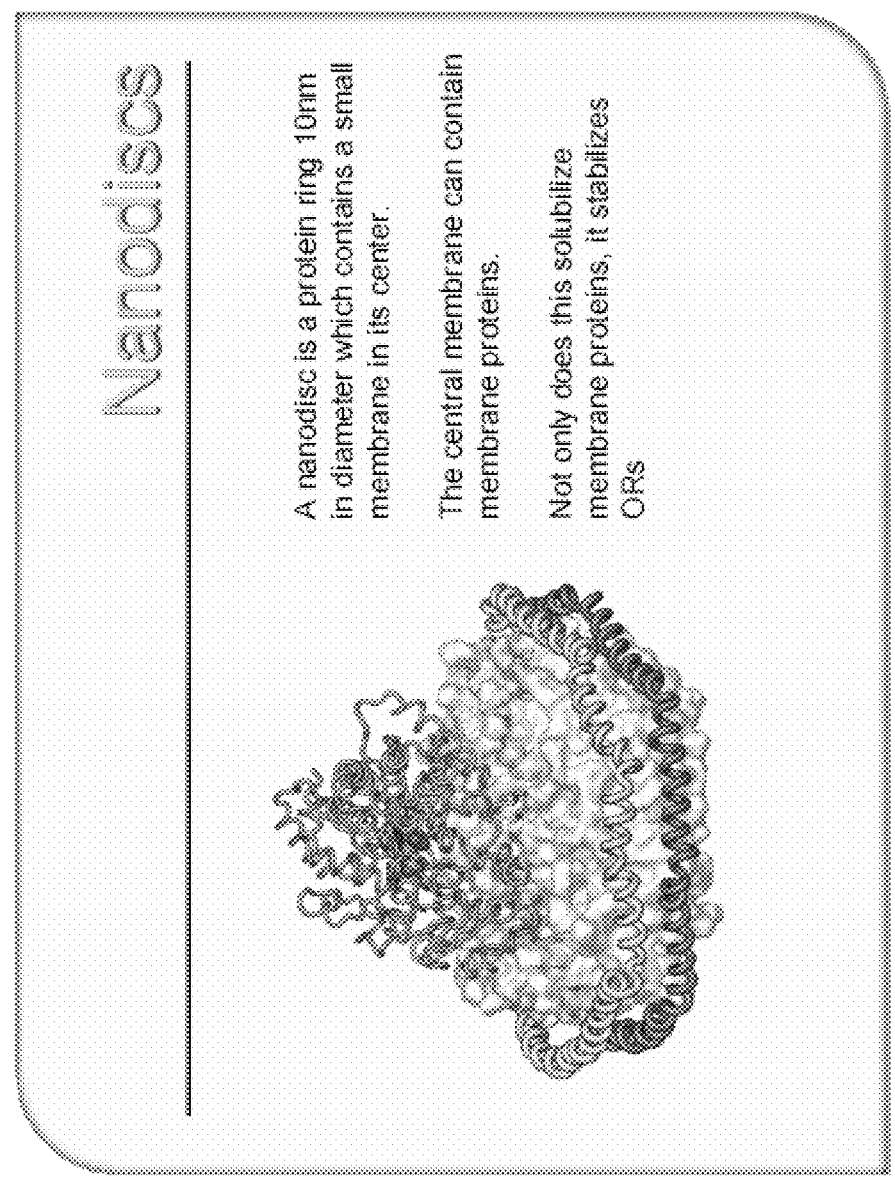
FIG. 17 depicts an exemplary nanodisc stabilizer.

An alternative strategy to produce vapor sensors entails solubilizing an OR with a more package known as a "nanodisc". Nanodiscs are engineered, self-assembling, disk shaped protein-lipid particles with well-controlled size and composition (E.g., Borch, Biol, Chem. 2009 August; 390(8). An exemplary nanodisc is shown in FIG. 17. Because the OR His-tag is exposed to the environment in this construct, it can also be attached to Ni-NTA functionalized nanotube transistors. OR-nanodiscs exhibited stability in solution. Digitonin solubilized mORs began to aggregate within hours (as confirmed by dynamic light scattering data), and were therefore attached to NT devices immediately following purification to minimize differences among prepared devices. The active lifetime of the constructed sensors is further described below.

While mORs (mouse-derived ORs) were used in certain of the non-limiting, illustrative embodiments described herein, the inventive devices and methods are applicable to virtually any membrane protein and a variety of other receptors. As described elsewhere herein, the devices and methods feature a membrane protein disposed in a lipid, amphiphile, or both, that allows the protein to maintain its natural conformation. In this way, the protein retains its natural sensitivity while also being integrated into a synthetic device, which device may be controllably assembled or even mass-produced.

Figure 15:
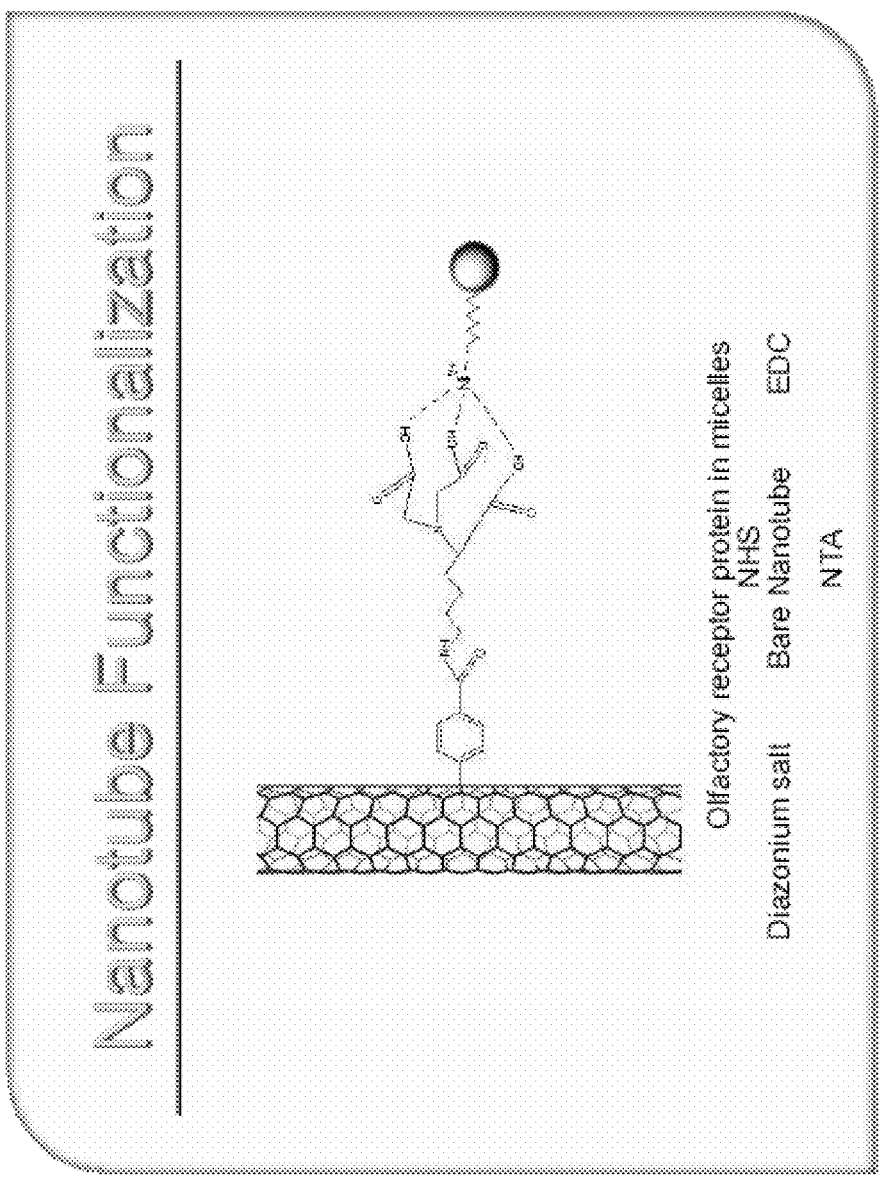
FIG. 15 depicts an exemplary nanotube functionalization.

Three-terminal transistor circuits were fabricated from carbon nanotubes grown on oxidized silicon substrates by catalytic chemical vapor deposition as described previously, with the heavily doped substrate used as a back gate electrode. Device current-gate voltage (I-$V_G$) characteristics at source-drain bias voltage $V_B$=100 mV were measured on a probe station under ambient conditions, and circuits that showed an on/off ratio exceeding 1000 were selected for use in subsequent experiments. Devices were functionalized with carboxylated diazonium salts, which spontaneously form covalent bonds to carbon nanotubes. A mild diazonium treatment was used, as excessive covalent modification of nanotubes impacts the semiconducting properties necessary for efficient signal transduction. The carboxylic acid functionality of the diazonium salt was activated with a standard EDC/sNHS treatment, followed by immediate attachment of the NTA linker. An exemplary linkage is shown in FIG. 15.

Chemical functionalization of the nanotubes was complete following the addition of Ni ions, which are chelated by the NTA complex. This treatment resulted in about 1 attachment site for each 150 nm length of exposed nanotube, as seen in FIG. 1B. Device fabrication may be accomplished by incubation in a solution of OR-containing digitonin micelles or nanodiscs, which allowed the His-tagged proteins to associate with the Ni-NTA attachment sites on the devices. A cartoon of the finished device is shown in FIG. 1C. That figure shows nanotubes having protein-containing micelles attached to the nanotubes. This attachment is suitably effected by interactions between a tag on the protein and a functional group on the nanotubes that is complementary to that tag.

Also shown in that figure are electrodes in contact with the nanotubes, allowing for application of current and monitoring of electronic characteristic of the device. The yield on this particular process from nanotube transistor to fully operational sensor was around 60%. While the Ni-NTA method was used in the exemplary devices described herein, virtually any pairing of protein tags and functionalities that create a bond or linkage between the semiconductor and protein is suitable. The bond/linkage between the protein and the semiconductor may be a direct linkage between the two, or there may be one or more molecules disposed between the protein and the semiconductor. The bond/linkage—whether direct or attenuated—suitably maintains the protein and semiconductor in electronic communication with one another. The bond/linkage may be ionic, covalent, or a coordination-type interaction.

Current-gate voltage ($I-V_G$) characteristics taken for a fixed source-drain voltage $V_B$ were used to monitor the effect of chemical functionalization on nanotube transistors. Typical $I-V_G$ curves starting with as-fabricated devices and following the functionalization process are presented in FIG. 1. The diazonium-Ni-NTA functionalization step leads to a slight decrease in the on-state current of the nanotube transistor, which may be ascribed to carrier scattering associated with covalent attachment of the complex to the NT sidewall.

The shift of the threshold voltage by approximately −1 V (from ~10V to ~9V) indicates that the Ni-NTA functionalization leads to a slight increase in positive charge in the nanotube environment, which is expected from exposure to nickel ions.

Addition of the OR-micelle results in a pronounced decrease in the on-state current as well as a more pronounced shift of the threshold voltage to negative values, both consistent with earlier work on protein-functionalized nanotubes. FIG. 1 shows a gate shift due to OR-micelle attachment; similar shifts are seen for attachment of ORs in nanodiscs.

Additionally provided are methods of assaying a sample. These methods may applied where the user seeks to determine what analyte or analytes are present in a sample. The methods are also applicable when the user seeks to determine the concentration of analyte in a sample.

Suitable samples include biological fluids, industrial fluids, vapors, and the like; the methods (and the inventive devices) are applicable to virtually any medium.

The methods suitably include contacting a sample, such as a liquid or vapor, with a sample with a device comprising a transmembrane protein disposed in a nanodisc, a lipid, an amphiphile, or both, the device comprising a semiconductor material in electronic communication with the transmembrane protein; and measuring a first electronic characteristic of the device when the device is contacted with the sample.

The transmembrane protein suitably interacts—e.g., by binding or complexing—with an analyte (such as an odorant) in the sample. As described elsewhere herein, GPCRs are considered especially suitable proteins for the claimed invention. In embodiments using GPCRs, the GPCR changes conformation upon binding or interacting with an analyte in the sample. The change in conformation may affects an electronic property of the protein-semiconductor device, and the change in electronic property may then be monitored or recorded.

The user may compare the exhibited, first electronic characteristic of the device (when exposed to the sample) to the value of that electronic characteristic corresponding to exposing the device to one or more known analytes. For example the user may compare the conductivity of the device ($C_1$) when the device is exposed to a sample that is suspected of containing cyclohexanone to the conductivity of the device ($C_0$) when exposed to cyclohexanone. Similar conductance values would then suggest that the sample contains cyclohexanone; differing conductance values would suggest that the sample does not contain cyclohexanone. A user may compile a library of one or more electronic characteristics of the device that correspond to the device's exposure to one or more known analytes, and then compare the devices electronic characteristics when exposed to unknown samples to that "library" to determine whether one or more analytes in the library is present in the unknown sample.

The methods may also be used to estimate the concentration of an analyte or analytes in a sample. As one example, the user may generate a calibration curve (or library) of the device's conductivity when exposed to known (or estimated) concentrations of cyclohexanone. The user may then expose the device to a sample containing cyclohexanone and compare the device's conductivity to the calibration curve and interpolate/extrapolate from the calibration curve to arrive at an estimated concentration of cyclohexanone in the sample.

Such devices allow for rapid-throughput screening of various analytes or even pharmaceutical candidates. As one non-limiting example, if a user's goal is to determine whether a compound (or compounds) are reactive (or non-reactive, in some cases) with a particular protein or receptor, the user can (1) construct devices according to the claimed invention that feature the protein/receptor of interest; and (2) assay the compounds of interest with the devices to determine whether the compounds under study interact (or do not interact) with the receptor or protein of interest.

The devices also, as described elsewhere herein, allow for assessment of the analyte content of a given sample. For example, a user may desired to determine whether a given sample (such as a biological sample or a water sample) contains toxins or contains other compounds at certain concentration levels. The user may then contact the sample with devices according to the claimed invention, which devices include receptors that are sensitive to the analytes of interest. Interactions between the analytes and the receptors will result in changes in an electronic characteristic of the device (such as conductivity), and the user can then correlate these changes (or lack of changes) in electronic characteristic to the presence (or lack of presence) of the analyte in the samples.

Additional Discussion

Vapor response measurements were performed on completed devices in a sealed environmental test chamber (see Additional Information, elsewhere herein). Gas flows containing odorant vapors of known concentration were created using a bubbler/mixing chamber system. Water vapor was added to the flow to create a relative humidity of 50%, which was found to be necessary for stable sensor operation. High purity nitrogen was used as a carrier gas and to flush the device between exposures to odorant-containing gas flows. In typical experiments, devices were loaded into the test chamber and allowed to equilibrate with a flow of nitrogen at 50% relative humidity. The DC resistance in the hole conduction regime (the backgate is set to −3V from the threshold voltage) was then monitored as the device was exposed to gas flows containing vapor odorants for 100 seconds and then purged with nitrogen for 100 seconds. Five sensing cycles were used at each concentration of chemical odorant, and the measured response is seen as a change in DC resistance.

In typical carbon nanotube based sensors, changes in resistance are caused by enhanced or suppressed electron scattering or by shifts in the local electric field leading to a change in the effective gating of the transistor. Nanotubes that are not functionalized with mORs, but are treated with Ni-NTA and surfactant, do not show changes in resistance when exposed to these odorants (FIG. 6), indicating the interaction of the odorants with the nanotube transistor is moderated by the mOR system.

Figure 2:
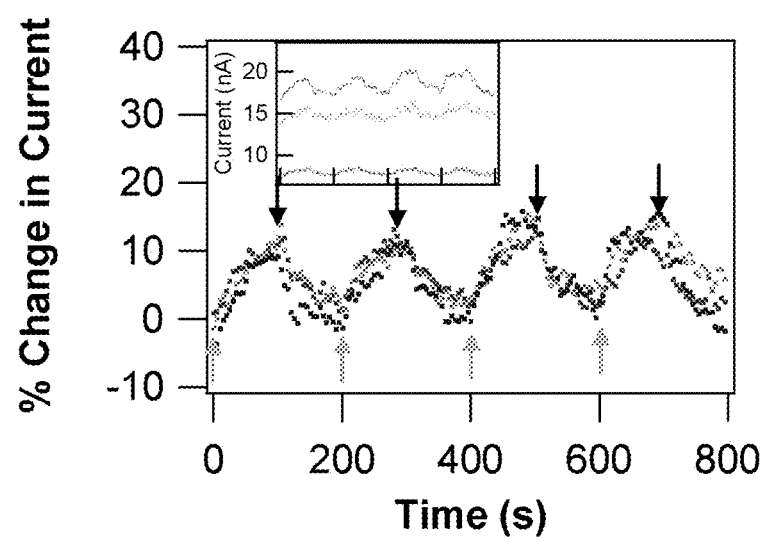
FIG. 2 illustrates three sets of vapor responses to eugenol at 2.1 ppm taken on consecutive days using a carbon nanotube modified with mOR174-9 in digitonin micelles—eugenol vapor was introduced every 200 seconds, as shown by the up-pointing arrows, and flushed out each time after 100 seconds of exposure as shown by the down-pointing arrows, each set of measurements has a different baseline current (inset), but the relative changes in current fall within a 96% confidence interval.

One exemplary vapor response data set is shown in FIG. 2, for a device functionalized with mOR 174-9 in digitonin micelles. Measurements conducted in *Xenopus* oocytes indicated that this OR is sensitive to eugenol, a naturally occurring small molecule commonly derived from clove oil. The data clearly show a large positive sensing response to eugenol (i.e., increase in the device current), with rapid response and recovery to baseline on the scale of tens of seconds. In contrast, as-fabricated nanotube transistors and nanotubes modified with empty digitonin micelles show no change in conductance when exposed to eugenol vapor. Thus the sensing responses seen in FIG. 2 integrate ORs with a (nanotubes) transistor. Both positive and negative vapor responses were observed, depending on the identity of the mOR and odorant used.

Device to device variation, and gradual long-term drift in the baseline resistance of OR-functionalized nanotube circuits causes the resistance of useful devices to range from ~100 k$\Omega$-10 M$\Omega$. Resistance differences may (without being bound to any single theory) be accounted for by presenting sensing data as a percent change from the baseline current (% $\Delta I/I$), a common method for presenting nanotube sensing data. As shown in FIG. 2, this normalization corrects quite well for sample drift in an individual device over the course of several days. As is the case for ORs in vivo, sensor refreshing requires no special procedures beyond flushing the odorant from the chamber, with a complete return to baseline within 100 seconds. There was reproducibility in the magnitude and shape of the sensing response and recovery across multiple measurements (FIG. 2).

Figures 3A, 3B:
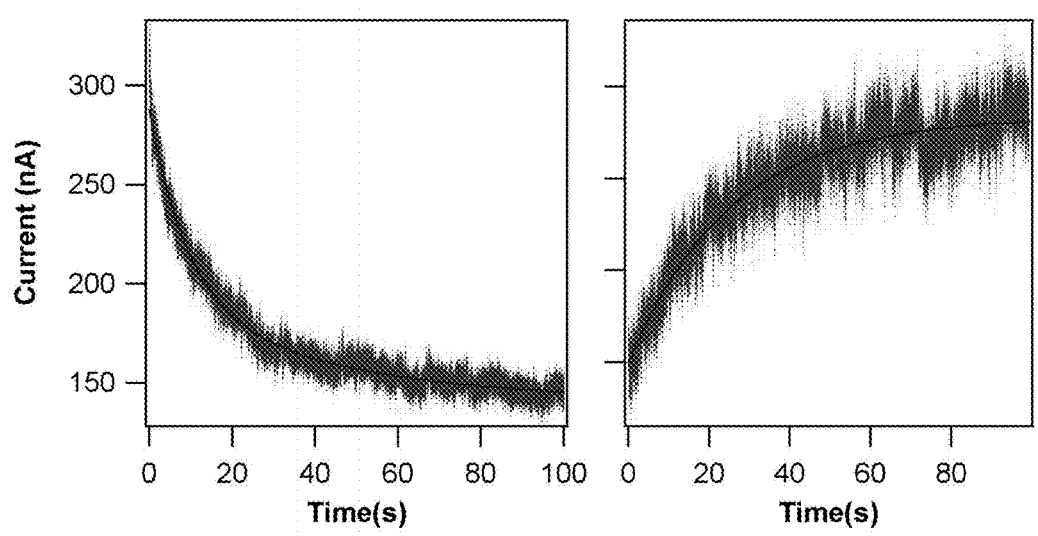
FIGS. 3A and 3B illustrate data with 0.2 ms time resolution for a nanotube device functionalized with mOR 256-17 in nanodiscs

A high-speed data acquisition system was used to investigate the shape and timing of the sensor responses. FIG. 3 shows the analysis of the response and recovery of a device functionalized with mOR 256-17 to cyclohexanone at 2250 ppm. Measurements in biological surrogates indicate that this OR is sensitive to a broad set of odorants, including cyclohexanone. The solid lines in FIG. 3 are fits to the sensing response and recovery data; individual data points are shown with dots.

Figure 7:
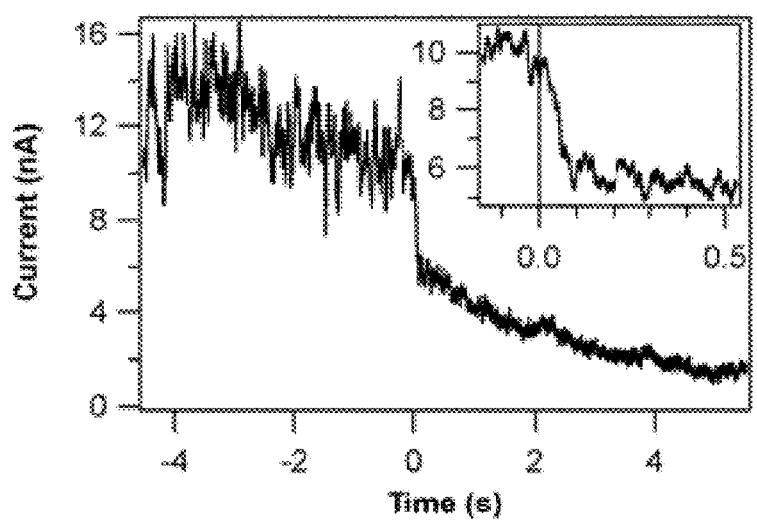
FIG. 7 illustrates the rapid sensing response of a single-stranded DNA transistor to DMMP in the same chamber as was used for the olfactory receptor experiments—the sudden response in the first 0.1 seconds was observed in several of the inventive devices.

To obtain a fit for the sensing response, it was effective to use a double exponential function with time constants of 9.08±0.04 and 41.2±0.4 seconds, while the signal on recovery can be fit with a single exponential with a time constant of 25.28±0.03 seconds. These times are typical of all the measurements, and there is no substantial difference between micelle and nanodisc sensing and recovery times. The observed timescales appear to be intrinsic to the OR-nanotube system, as it was verified that the response time for the measurement apparatus itself is less than 100 ms in separate experiments using DNA-functionalized nanotube devices (FIG. 7). The relatively slow response suggests—without being bound to any particular theory—a different sensing mechanism from typical carbon nanotube chemical sensors. The complex binding and release dynamics with more than a single time constant are typical of the biological olfactory system.

Figure 4:
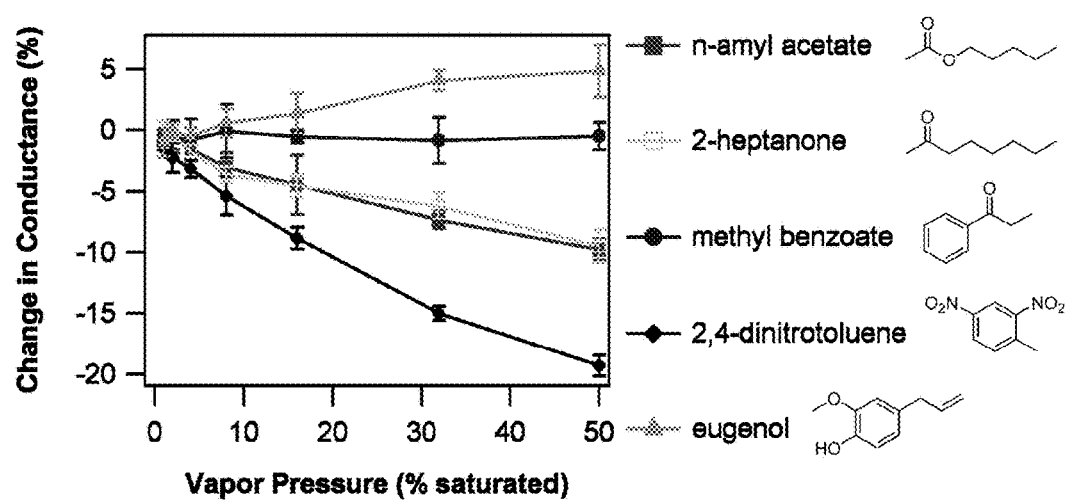
FIG. 4 illustrates sensing response versus concentration for five different odorants from a single sensor measured multiple times for each concentration-odorant data point. The nanotube in this sample was functionalized with mOR203-1 in digitonin micelles. A range of different responses is shown here, including positive changes in conductance (eugenol), no change in conductance (methyl benzoate) and negative changes in conductance (n-amyl acetate, 2-heptanone and 2,4-dinitrotoluene)

Sensing measurements such as that shown in FIGS. 2 and 3 have been done for a range of different concentrations. At each concentration, the sensing chamber is exposed to an odorant and flushed with inert gas multiple times. A comparison can be made between the relative changes in conductance for each concentration; a clear concentration dependent response can be seen. Data from such a series of experiments is shown in FIG. 4. To account for different vapor pressures, the data is plotted against the percent vapor pressure relative to saturated vapor for each odorant. Shown in this way, clear concentration dependence can be seen simultaneously for many different odorants from a single sensor. This ability to sense multiple chemicals in one sensor is a fundamental quality necessary for a practical general chemical sensor and is consistent with the behavior of ORs, which are broadly tuned, and able to recognize a wide range of different compounds with varying degrees of specificity. Thus, the present invention enables the user to assay a sample for the presence of multiple analytes.

The device used in FIG. 4 was functionalized with the third mouse olfactory receptor used here, mOR 203-1. Oocyte measurements show sensitivity of this protein to 2-heptanone, a mouse pheromone. FIG. 4 demonstrates that the mOR 203-1 functionalized carbon nanotube device has concentration dependent responses and is sensitive to 2-heptanone, as well as several other odorants.

In particular, the responses from the inventive devices to 2-heptanone and n-amyl acetate are very similar. Chemically, these two compounds are related: 2-heptanone is a methyl ketone with a five-carbon chain, while n-amyl acetate is an acetate ester with a five-carbon chain. As a result of their similarity, these odorants are qualitatively alike to humans. Additionally, both of these chemicals are known mouse pheromones, and produce similar neural excitations in the mouse main olfactory bulb. The similar response from 2-heptanone and n-amyl acetate may indicate that they have the same effect on this olfactory receptor when attached to a surface.

The other three odorants shown in FIG. 4 are all benzene ring based structures. Despite some basic structural similarities among those three odorants, the responses of all three are different. The response to eugenol is a positive change in conductance, while methyl benzoate results in no change and 2,4-dinitrotoluene results in a negative change in conductance larger than that seen for the mouse pheromones. Of the five odorants shown in FIG. 4, 2,4-dinitrotoluene is the only one not found in nature. Functionalizing the inventive devices with a naturally occurring protein has created a sensor which can detect this man-made explosive. It is not known whether mice can smell DNT, but evidence suggests that bomb detecting dogs and rats can. One feature of the biological chemical sensing system is the ability to quickly learn new scents, even those for which there was never any evolutionary pressure to detect. This is a skill which still eludes electronic chemical sensors, but has been an active area of research.

Figure 5:
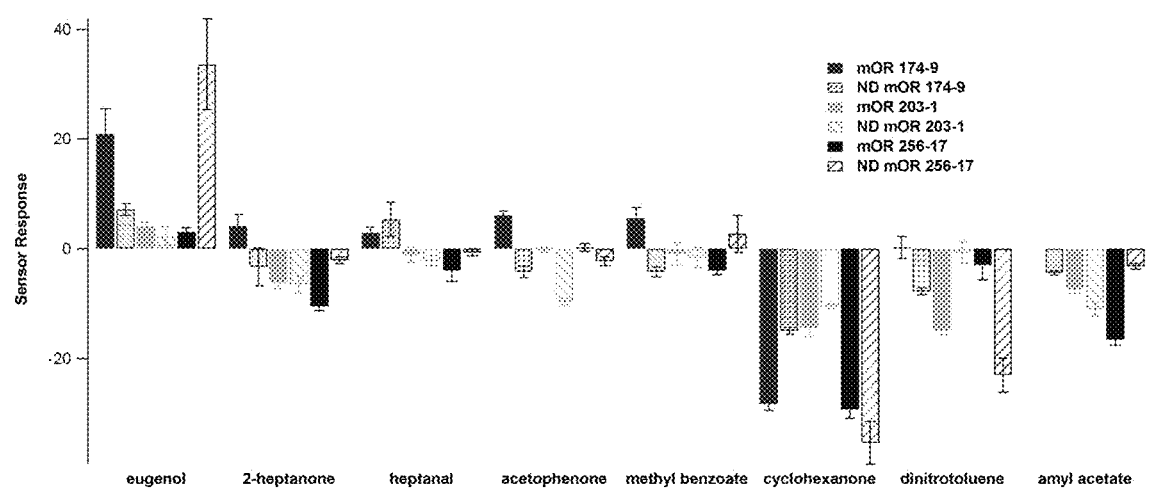
FIG. 5 illustrates sensor responses at 32% saturated vapor for various tested odorants and various fabricated devices.

Each of the three proteins described here were tested against a number of odorants, using both the surfactant stabilized and nanodisc stabilized forms. The results are summarized in FIG. 5. FIG. 5 represents responses from 16 successfully functionalized sensors measured against the 8 odorants several times, and includes over 400 measurements. Control devices that contain no proteins showed no sensing response.

It is unclear whether the biological function of the attached protein or some quirk of the attachment process is responsible for all of the sensing responses seen in FIG. 4 and FIG. 5. There are only around 1000 olfactory receptors used to trigger smell in the mouse olfactory bulb, yet there are far more than 1000 odorants which mice can detect. Necessarily, each olfactory receptor will bind multiple chemicals, and the combination of responses leads to a differentiating signal It is also likely that there are chemicals which will bind to olfactory receptors which do not trigger a biological response, but which will trigger a response in this electronic system.

For example, the inventive devices show a strong response to cyclohexanone. Oocyte measurements show a response to cyclohexanone by mOR 256-17, but not for either of the other proteins. It is possible that the cyclohexanone response is due to a different mechanism than that which is responsible for smell.

Complicating interpretation of these results, the oocyte experiments used to test the chemical sensitivity of mouse olfactory receptors were performed in an aqueous environmental media, and hence, imperfectly replicate the mouse olfactory bulb. It is worth considering whether some of the additional electronic responses make sense from a biological perspective.

Figure 18:
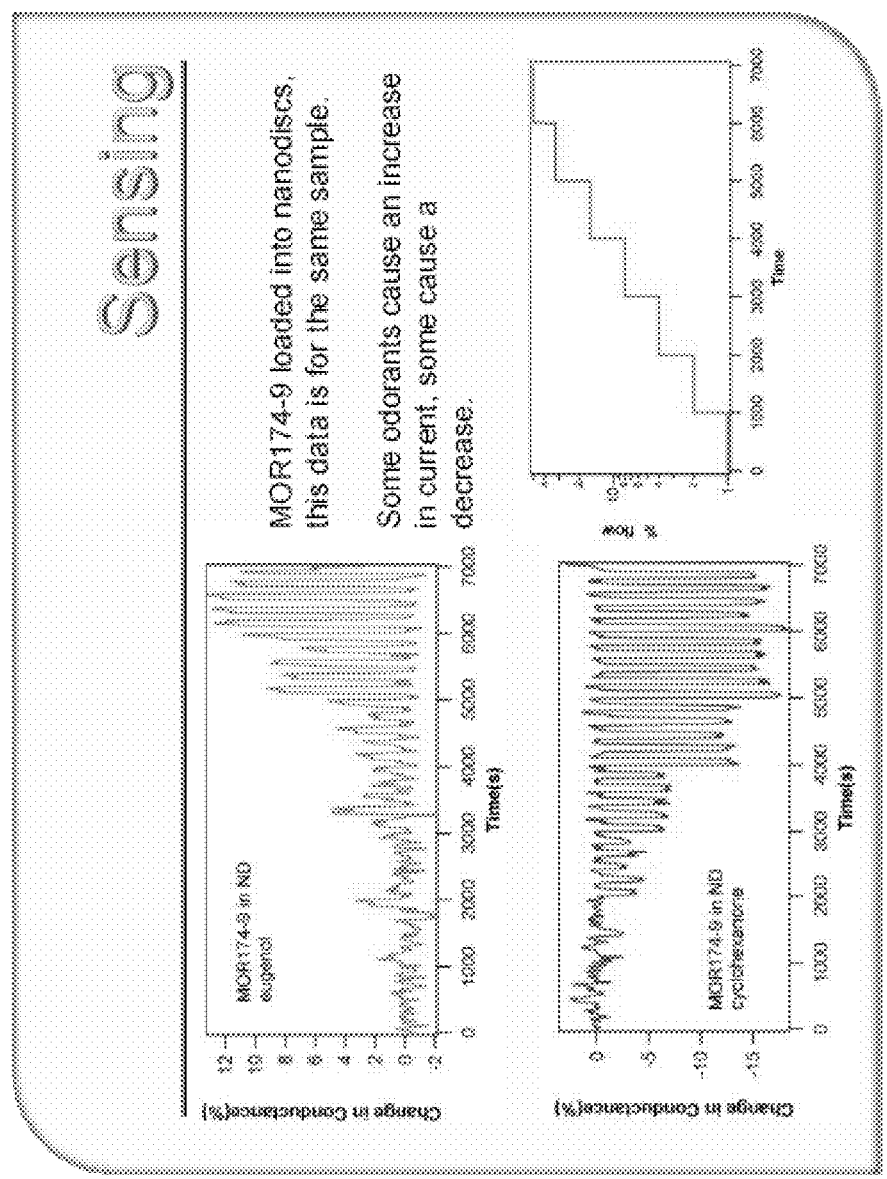
FIG. 18 depicts illustrative data from nanodisc-stabilized devices.

There are certain similarities and differences between the surfactant stabilized and nanodisc stabilized proteins. For both types of packaging, mOR 174-9 shows the expected response to eugenol, e.g., FIG. 18. The only other response shared between the two packaging methods for this protein arises following exposure to cyclohexanone. mOR 203-1 has very similar responses for 6 of the 8 odorants tested with both packaging methods, including the expected response to 2-heptanone.

Additional exploration involving olfactory receptors and GPCRs will further distinguish which aspects of the sensing response are due to a particular olfactory receptor, a class of olfactory receptors or protein modified nanotubes in general. Understanding the structure and function of GPCRs is an ongoing area of research. This work establishes the future promise of hybrid bio-nano electronic devices in this area and positions these types of devices to advance in step with molecular biology.

Figure 8A:
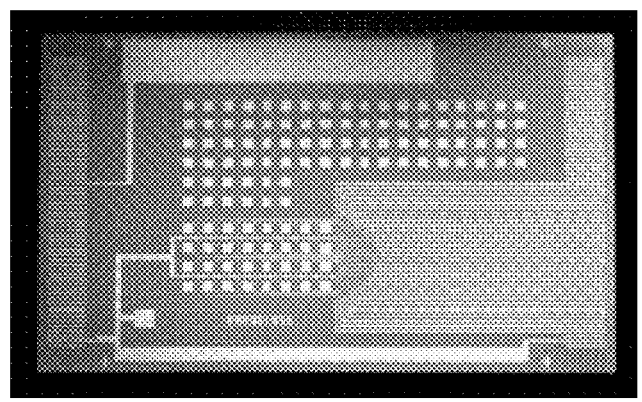
FIG. 8A illustrates an image of the arrayed device used to test the ability to scale up fabrication of olfactory receptor functionalized nanotube transistors using commercial techniques.
Figure 8B:
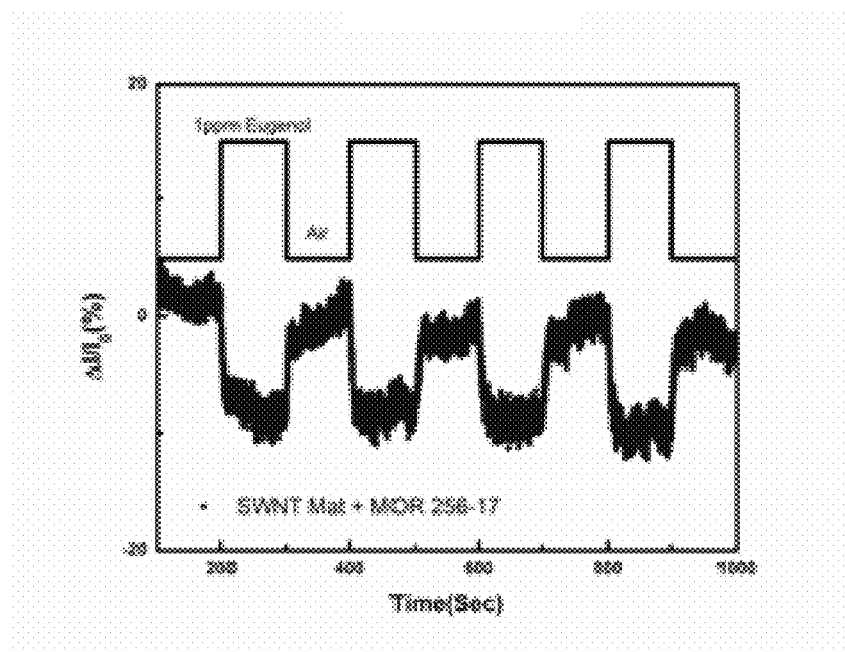
FIG. 8B illustrates the sensing response to one such device using eugenol—sensing data is percentage change from the background current.

Arrays of the inventive devices may be fabricated; arrays of 32 mOR functionalized nanotubes have been fabricated in a process designed to work with commercial, highly multiplexed electronics (FIG. 8A). These arrays, which may be constructed with lipids, amphiphiles (e.g., digitonin), nanodiscs, or both, functioned as the isolated devices described here, even when using air instead of nitrogen as the carrier gas (FIG. 8B). As described elsewhere herein, receptors may be sensitive to multiple analytes. By arraying receptors of the same or different variety, a user may assemble devices having sensitivity to a wide range of analytes. This enables the construction of one-size-fits-all devices that allow a user to contact the device to a sample and to then detect virtually any analyte to which the receptors are sensitive.

Thus, the present invention includes successfully modifying an existing bio-functionalization scheme for carbon nanotubes to allow the attachment of membrane proteins. The sensing measurements demonstrate that a protein with known sensing properties can be coupled to an electronic device and transfer some of those sensing properties to the device. This is the first demonstration of a vapor sensor using proteins, and one of the most advanced integration of GPCRs with electronics to date. The process disclosed here is extendable to other G-protein coupled receptors aside from mORs, and can be generalized to virtually any protein or other biological structure that normally resides in a lipid or amphiphilic environment.

Supplemental Information

Materials and Methods

Mouse Olfactory Receptor Expression

Recombinant mouse olfactory receptors (mOR) 174-9 and 203-1 were expressed in Sf9 insect cell system using the BaculoDirect Expression System (Invitrogen). The entry clones for mOR 174-9 (Olfr73; BC141607) and 203-1 (Olfr992; BC141642) were from Invitrogen. The DNA sequence of each receptor was verified using primer pairs specific to each receptor. The DNA sequence of both mOR 174-9 and mOR 203-1 clones were verified using GW1 forward primer (GTTGCAACAAATTGATGAGCAATGC (SEQ ID NO: 1)) and GW2 reverse primer (GTTGCAACAAATTGATGAGCAATTA (SEQ ID NO: 2)).

The entry clones were used to create an expression clone for each mOR through Linear Recombination (LR) reaction using BaculoDirect Linear DNA with a N-terminal His tag. Two recombinant expression clones were created: mOR 174-9 with N-terminal His tag, and mOR 203-1 with N-terminal His tag. All expression clones were used individually to transfect Sf9 insect cells. Six days after transfection, the cells demonstrated signs of infectivity. The viral stock was collected and was labeled P1 viral stock. The P1 viral stock was stored at ~80° C. in the dark with 10% fetal bovine serum (FBS) to protect the recombinant virus from proteases. A second and third round of viral amplification were performed and labeled P2 and P3 viral stocks, respectively. An aliquot of P3 viral stock was collected and used to isolate and purify the viral DNA for PCR to check the orientation of the mOR DNA fragment after transfection and expression.

The viral titer of all P3 viral stocks was determined following the protocol on BacPAK™ Baculovirus Rapid Titer Kit (Clontech). Once the viral titer was known, Baculovirus Infected Insect Cell (BIIC) stock was prepared for each recombinant mOR. BIIC stock was found to be more stable than the viral stock. BIIC stock with multiplicity of infection (MOI) of 3 was prepared based on the methodology by D. J. Wasilko and S. E. Lee (2006, Bioprocessing Journal, 29-32). Sf9 cell culture was infected with BIIC stock to express the recombinant mORs. The expression of all recombinant mORs was monitored by determining the % viability, total cell density and viable cell density during the infection process. A decrease in % viability and increase in both the cell diameter and viral titer can be observed during infection. While still in their log phase state, the cells were harvested, as the % viability of the Sf9 culture reached 70-80%.

Purification of Mouse Olfactory Receptors: Preparation of the Crude Plasma Membrane Fraction (CMF).

Sf9 cells infected with mOR 174-9 and 203-1 were harvested by centrifugation (1,000×g, 10 min, 4° C.) when the cell density was about $0.5 \times 10^7$ to $1 \times 10^7$ viable cells/mL. The pellets were washed initially by resuspending in a concentration of phosphate buffered saline (PBS) equivalent to the osmolality of the cell growth media and centrifuged (1000×g, 10 min, 4° C.). The pellets were resuspended in a lysis buffer consisting of 20 mM Tris-HCl (pH 8.0) 1 mM EDTA, 1 mM EGTA, 0.4% (v/v) ethanol, 0.1 mM PMSF, and protease inhibitor cocktail designed for Sf9 cells (Sigma) and homogenized with a Dounce homogenizer (pestle A, 0.0030-0.0060 in.). In some cases, such as when there was a large amount of nuclei present in the homogenate (as evident from the presence of a clear jelly-like substance), the homogenized cell suspension was centrifuged (300×g, 10 min, 4 deg. C.) to remove the more dense nuclei and unbroken cells. The homogenate, or supernatant in the case of the latter, was then centrifuged (40,000×g, 20 min, 4 deg. C.) and the supernatant discarded. The pellets were resuspended in a solution of 20 mM Tris-HCl (pH 8.0), 3 mM MgCl2, 0.5 mM CaCl2, and 10 ug/mL deoxyribonuclease (DNase)-I, and centrifuged (40,000×g, 20 min, 4 deg. C.). The supernatant was discarded, and the pellet was resuspended in approximately 400 microliters of 20 mM Tris-HCl (pH 8.0), 3 mM MgCl2, 0.5 mM CaCl2, and 10 ug/mL deoxyribonuclease (DNase)-I per 30 mL of cells harvested (ca. 0.75 mg total protein/mL cells harvested), using a 5 mL Wheaton homogenizer. Resuspended pellets were then aliquotted into Eppendorf tubes, flash frozen in liquid nitrogen, and stored at −80° C.

Purification of Mouse Olfactory Receptors: Nickel Bead Purification

A 400 uL aliquot of CMF was solubilized in a solution such that its final composition was 6.76 mM Digitonin, 19 mM NaH2PO4, 115 mM NaCl, 12 mM Tris, 2 mM MgCl2, 0.3 mM CaCl2, and 6.2 ug/mL DNase-I. Solubilization of the CMF was achieved via agitation on a benchtop vertical rotator for 1 h, or via sonication with a microtip (Misonix Ultrasonic Liquid Processor). PureProteome™ Nickel-magnetic beads (Millipore) were added to the solubilized CMF in a volume of 50 mM NaH2PO4, 300 mM NaCl, pH 8.0, such that the final concentration of digitonin was 4.88 mM. The Ni-magnetic beads were mixed with solubilized CMF for 1 h at 4° C. on a vertical rotator and isolated with a magnet. The His-tagged protein was eluted from the beads with approximately 1.25 mL of 4.88 mM digitonin prepared with 100 mM acetate buffer (pH 4.0), and the pH was adjusted to 8.0 using a micropH electrode. The pH adjustment typically required no more than 0.2 mL NaOH. Note: Although western blots performed on the proteins eluted from the Ni-magnetic beads indicated the purification of mORs was successful, other data indicate a significant amount of protein remained on the beads, which could not be eluted using standard elution methods (e.g., pH 4.0 buffer, 300 mM imidazole, exchanging Digitonin with CHAPS).

Carbon Nanotube Transistor Fabrication

Carbon nanotubes were grown on p++ doped silicon wafers with 500 nm thermal oxide from Silicon Valley Microelectronics. Approximately 5 mL of 50 mg/L iron nitrate solution was spun onto wafers at 2000 RPM until dry to provide growth catalyst. Wafers were broken into halves and annealed at 910 deg. C. for 15 minutes. Growth was performed in a 50 mm tube furnace at 910 deg. C. in a flow of 2500 sccm methane and 320 sccm hydrogen with 600 sccm Argon as carrier gas for 10 minutes. The furnace temperature was then decreased to 100 deg. C. over approximately 2 hours in a flow of 320 sccm hydrogen with 600 sccm argon before samples were removed from the furnace.

Nanotube transistor fabrication was carried out using optical lithography. PMGI (Michrochem SFS2) was spun on at 4000 RPM for 45 seconds and samples were baked at 150 deg. C. for 5 minutes. Photoresist (Shipley 1813) was spun on at 5000 RPM for 45 seconds, and samples were baked at 115 deg. C. for 1 minute. After an exposure of about 100 mW/cm2, Microposit MF-319 was used to develop for around 1 minute.

5 nm chrome and 50 nm gold was deposited in a home-built thermal evaporator. Liftoff was done in an acetone bath, followed by a bath in Microposit Remover-PG to remove the PMGI, then multiple clean water baths.

The resulting devices have a 2 micron source-drain distance. Before electrical measurement, chips were baked at 250 deg. C. in air for 30 minutes to remove residual residue from fabrication. Typical nanotubes are single walled and between 1.0 and 2.5 nm in diameter. Typical devices have 1 to 3 nanotubes bridging the gold electrodes. Electrical data, using the silicon wafer as a transistor back-gate, is gathered on all devices before chemical modification.

Chemical (Ni-NTA) Modification of Carbon Nanotubes

Carbon nanotube transistors on silicon wafers were chemically functionalized using a procedure similar to that described by Graff et al. All solutions were prepared using deionized water with an electrical resistance of 18.2 MΩ-cm. All chemical modifications were performed on the chips in 50-mL polypropylene Falcon tubes. First, samples were placed in a solution of 10.76 mM 4-carboxybenzene diazonium tetrafluoroborate at 45 deg. C. for 1 h, followed by washing with acetone, methanol, and water. The chips were then placed in a solution of 2 mM EDC, 5 mM Sulfo-NHS, prepared with activation buffer (0.1 M 2-(N-Morpholino)ethanesulfonic acid (MES) sodium salt, 0.5 M NaCl, pH adjusted to 6.0 with HCl) at room temperature for 15 minutes to activate the carboxylic acid of the 4-carboxybenzene covalently attached to the nanotubes. Immediately afterwards, the chips were briefly dunked in activation buffer and placed in a solution of 11.3 mM NTA-NH2 prepared with phosphate buffered saline (PBS; 0.1 M NaH2PO4, 0.15 M NaCl, pH adjusted to 7.35 with NaOH) for 2 h. Upon completion, the chips were washed with water and placed in a solution of 11.3 mM $NiCl_2$. After 1 h, the chips were removed from the $NiCl_2$ solution, washed with water, and stored in 25% (v/v) ethanol, at 4 deg. C.

Attachment of mORs to Ni-NTA Modified Nanotubes

Chips containing Ni-NTA modified nanotubes were removed from storage in ethanol, rinsed in water, and dried in a stream of high purity nitrogen or argon gas. A solution containing mORs prepared as described above was deposited on the surface of the chips for 30 min, at room temperature. A large enough volume was deposited on the chips such that any volume change over the 30 min period due to evaporation was negligible. If the solution used was surfactant stabilized mORs, the chips were then rinsed with a 1 mM digitonin solution. If the solution used was nanodisc stabilized mORs, the chips were rinsed with water. All samples were dried in a stream of nitrogen or argon gas.

Sensing Apparatus

The temperature, humidity, flow rate and flow paths are controlled by a computer. The computer also communicates with and controls a Keithley 6485 which measures the current through the device. A digital acquisition card provided the 100 mV source-drain voltage and is connected to the analogue out of the Keithley 6485 to record high time resolution current data. The gate was controlled by a Keithley 617.

MKS 1179A style mass flow controllers are used to create three flows of nitrogen. One steady flow of 1000 sccm is bubbled through water to provide a humidified stream of gas. The "sample flow" is switched between a bubbler containing the odorant being tested and a bypass which is not exposed to any odorant. The last flow serves as a "background" to further dilute the sample flow. The "sample" and "background" flows are set so that they add up to 1000 sccm total flow. These three flows (humidity, sample and background) are combined and then fed into the sensing chamber. Throughout the measurement, the total flow rate, temperature and humidity do not change.

The chips sit in a stainless steel sensing chamber, with gold pogo pin contacts to the interrogated devices. The total volume off the sensing chamber is around 40 mL. Tubing, fittings, valves and the chamber are cleaned by rinsing with acetone, isopropyl alcohol and water, followed by baking for around 1 hour at 150 deg. C.

Chemical Analytes

All odorants used are liquids under ambient conditions except for 2,4-dinitrotoluene, which is a solid. Carrier gas was bubbled through liquid odorants and forced through a column containing compressed powder of 2,4-dinitrotoluene. Analytes were used in pure form.

Control Measurements

Figure 6:
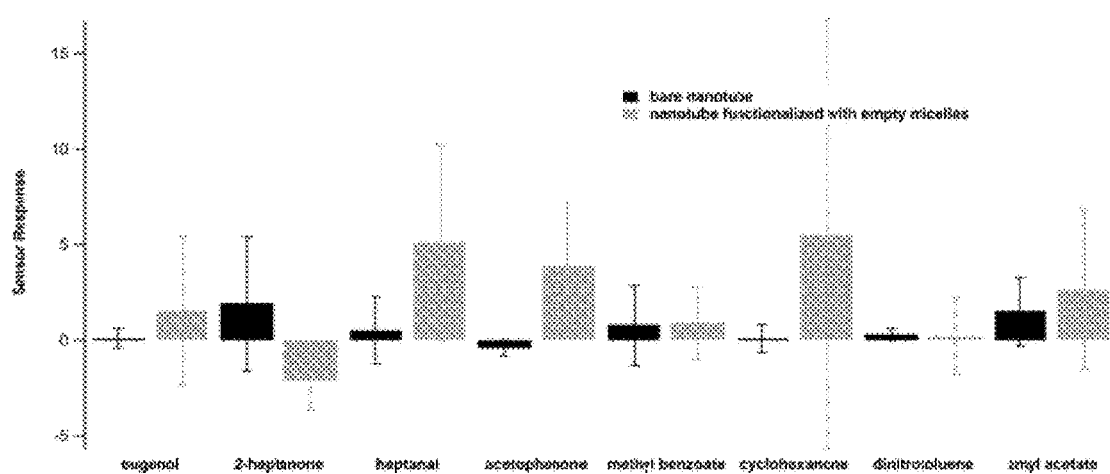
FIG. 6 illustrates bare nanotube and micelle-functionalized nanotube responses at 32% saturated vapor for all of the odorants tested—the data scale here is smaller than that of FIG. 5.

All odorants were tested against bare nanotubes, showing no response, as seen in FIG. 6. All odorants were tested against nanotube devices which had been nearly properly functionalized, but the olfactory receptor was left out of the final step. The resulting devices are nanotubes chemically modified with NTA and also decorated with occasional noncovalently bound digitonin micelles. These devices show some additional environmental sensitivity, but do not function as "sensors." No clear sensitivity to any of the odorants was seen.

Sensing Speed

The chemical sensing chamber used for these experiments is described in detail above. The gas introduction and flushing speed has been well characterized over several years of chemical sensing measurements on functionalized carbon nanotubes and graphene. Here is shown an example of a sensor response using carbon nanotube devices which have been functionalized with single stranded DNA. Other than the chemical treatment of the nanotube device and the odorant used, there is no physical difference in the sensing chamber configuration. The chemical being sensed here is DMMP, which is similar in size to the odorants tested in the paper.

Arrayed Devices

The chip in FIG. 8A has 32 nanotube transistors on it with a common drain, and common back gate. The chip was interfaced with custom electronics through flexible printed circuits (flex tabs) to a highly parallel commercial sensing system. Fabrication was done on a 4" wafer using a commercialized 6" CVD furnace system to grow carbon nanotubes.

Data was collected as in the paper. Eugenol vapor was generated by bubbling breathing grade air, and then mixing with breathing grade air. The precise concentration of Eugenol was verified using an FTIR spectrometer. The total flow rate was maintained at 1000 sccm throughout flush and gas delivery cycles.

Additional Non-Limiting Embodiments

Three mouse olfactory receptor proteins (mORs) were selected for overexpression and integration with NT transistors for vapor response testing against a panel of 8 odorants: mOR174-9 (also known as mOR-EG) is known to respond to eugenol; mOR203-1 and mOR256-17 respond to 2-heptanone and cyclohexanone, respectively. Two of these mORs (174-9 and 256-17) were screened with a panel of 8 odorants using a Xenopus oocyte expression system in combination with robotic electrophysiology. The third mOR (203-1) did not express well in the Xenopus oocytes, however similar information is available from expression in human embryonic kidney (HEK) cells from others. FIG. 13 (Table I) summarizes response characteristics of the three mORs when expressed in heterologous surrogates and also when coupled to the electronic system described in this paper. The response characteristics of ORs are known to be broadly tuned, so that individual ORs recognize a range of different odorants with varying degrees of specificity.

That table shows responses of mouse olfactory receptor proteins (mORs) to selected odorants, in biological and electronic systems. For NT devices, responses are reported as percent change in the device current upon exposure to 32% of a saturated vapor. For the heterologous systems, data is presented as EC50 values on a logarithmic scale. EC50 is the concentration of analyte in solution necessary to produce a signal 50% of the magnitude of the saturated signal. Thus, the number in the table is $2*\text{Log}[M]$ where [M] is the molarity of the analyte solution that gives a 50% response.

Recombinant mORs were expressed with an N-terminal His-tag in Sf9 insect cells to simplify the purification and guide the attachment of ORs to carbon nanotube devices. After harvesting the cells, target mORs were purified using magnetic beads treated with Ni-NTA. The presence and correct molecular weight of the protein after the purification was verified by Western blot. Throughout all stages of the purification process, the protein was maintained in ~4.88 mM (0.6% w/v) digitonin, a surfactant containing a cholesterol-like backbone that promotes functional solubilization of membrane proteins. At concentrations above 0.5 mM, digitonin forms micelles that can house and solubilize individual ORs in a membrane-like environment. In a second approach, ORs were embedded in soluble "nanodiscs", disk shaped protein-lipid particles designed to self-assemble with well-controlled size and composition. Consistent with previous accounts of nanodisc behavior, mOR-nanodiscs exhibited significantly enhanced stability in solution, with a shelf life of several months. In contrast, digitonin solubilized mORs would aggregate within hours, as confirmed by dynamic light scattering measurements (data not shown), so these solutions were used to functionalize NT devices immediately after purification.

Figures 10A, 10B, 10C:
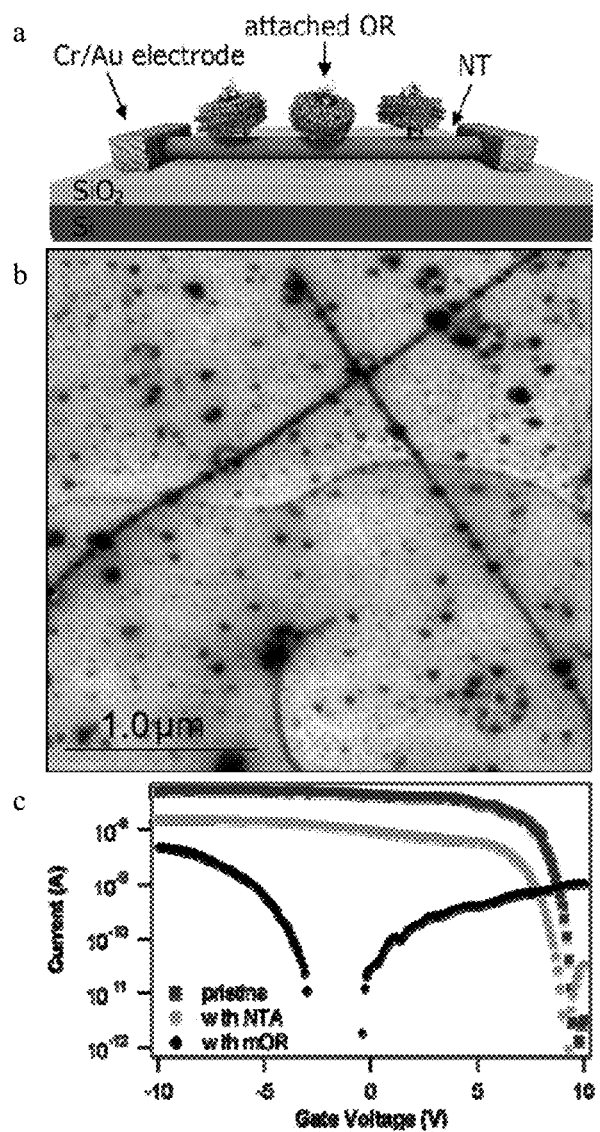
FIGS. 10A-10C illustrate carbon nanotube devices functionalized with mouse olfactory receptor proteins (mORs)

Three-terminal transistor circuits that acted as readout elements of OR-odorant binding were fabricated from carbon nanotubes (NTs) grown on oxidized silicon substrates by catalytic chemical vapor deposition as described previously. Device current-gate voltage ($I$-$V_G$) characteristics were measured under ambient laboratory conditions, and circuits with an on/off ratio exceeding 1000 were selected for use in experiments. Devices were functionalized with carboxylated diazonium salts, which readily form covalent bonds to NTs. As detailed in Materials and Methods, a mild diazonium treatment was used, since excessive covalent modification of NTs destroys the semiconducting properties necessary for efficient signal transduction. The carboxylic acid functionality of the diazonium salt was activated with 1-ethyl-3-[3-dimethylaminopropyl]carbodiimide hydrochloride/sulfo-N-hydroxysuccinimide (EDC/sNHS) treatment, followed by attachment of the NTA linker. This treatment provides ~5-10 attachment sites for each 1 µm length of exposed nanotube (FIG. 10A). Device fabrication was completed with the addition of Ni ions, which are chelated by the NTA complex, and incubation in a solution of mOR-containing digitonin micelles or nanodiscs. This treatment allowed the His-tagged proteins to associate with the Ni-NTA attachment sites. FIG. 1B is a schematic of the finished device.

Control experiments were conducted using identical incubation and washing protocols to confirm that binding between mORs and the nanotube was controlled by the Ni-NTA:His-tag interaction. It was confirmed that empty digitonin micelles and empty nanodiscs have no affinity for Ni-NTA modified nanotubes. Ni-NTA functionalized devices were also exposed to proteins without His-tags and confirmed that no bound proteins remain after the wash protocol. The proteins for these experiments were commercially obtained protein G. The experiments did not use the mORs since these were all His-tagged, and were not designed for His-tag removal. Without being bound to any particular theory, the control experiments are thus consistent with the hypothesis of (oriented) protein attachment via the expected chemical bond between the Ni-NTA functionalized nanotube and the protein's His-tag.

Current-gate voltage ($I$-$V_G$) characteristics were used to monitor the effect of chemical functionalization on performance characteristics of nanotube transistors. FIG. 10C shows a typical I-$V_G$ curve of an as-fabricated device and its evolution through the functionalization process. One may assume that the mechanism underlying changes in NT conduction is dominated by electrostatic coupling to the local environment. Shifts in threshold gate voltage for conduction are attributed to changes in the charge in NT environment, while changes in the on-state current are assumed to reflect changes in carrier scattering. Ni-NTA functionalization leads to a ~3-fold decrease in the on-state current of the NT, which is ascribed to carrier scattering due to covalent attachment of the complex to the NT sidewall. The observed threshold voltage shift of −1 V (from ~10V to ~9V) indicates that Ni-NTA functionalization leads to slightly increased positive charge in the nanotube environment, which is associated with the 2+ charge of the nickel ions. Addition of mOR-micelles results in a pronounced decrease in the on-state current and a strong negative shift of the threshold voltage, both consistent with earlier work on protein-functionalized NT transistors. Similar shifts in threshold and resistance are seen for devices functionalized with mOR-nanodisc constructs.

Responses of NT devices to odorant exposure were measured in a sealed environmental test system through which gas flows containing known concentrations of odorant vapors were passed (see Materials and Methods for details). High purity nitrogen served as a carrier gas for the odorants and to flush the device between exposures to odorant-containing flows. A humidified environment was useful for device stability, so water vapor was added to all flows to create a relative humidity (RH) of 50%. Devices under test were loaded into the chamber and allowed to equilibrate in a flow of nitrogen at 50% RH. The devices were put into the hole conduction regime by setting the back gate voltage 3V below the threshold voltage, and the DC resistance was monitored as the device was exposed to gas flows containing odorants for 100 sec and then 50% RH nitrogen for 100 sec. Five sensing cycles were used at each odorant concentration to quantify response reproducibility. The response is reported as a fractional change in DC current at constant bias voltage. In NT transistors, changes in resistance due to chemical interactions are caused by shifts in electron scattering or in the effective gating of the transistor, both of which are likely to occur in the odorant-protein-nanotube system.

Characteristics of the odorant responses of mOR-functionalized devices are shown in FIG. 11. FIGS. 11A-11B illustrate large positive responses to eugenol (i.e. increase in device current), consistent with strong responses observed in *Xenopus* oocytes expressing the same OR. NT devices have rapid and reproducible responses and full recovery to baseline on the scale of seconds (FIG. 11C). As is true for ORs in vivo, refreshing the device requires no special procedures beyond flushing the odorant from the chamber. Differences in device properties can be normalized by presenting sensor responses as a percent change from the baseline current (% ΔI/I). This normalization can correct for device-to-device variation as well as slow drift in a single device over several days (FIG. 11B).

Figure 11A:
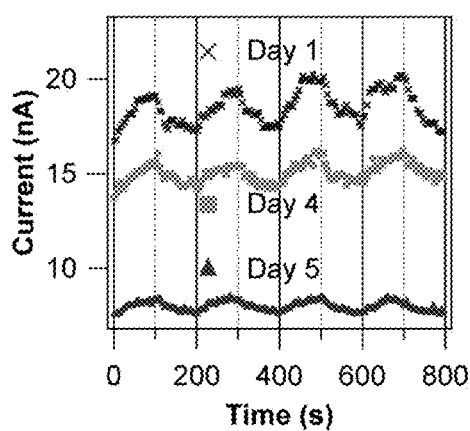
FIGS. 11A-11D illustrate odorant responses of carbon nanotube (NT) devices functionalized with olfactory receptor proteins (ORs).
Figure 11B:
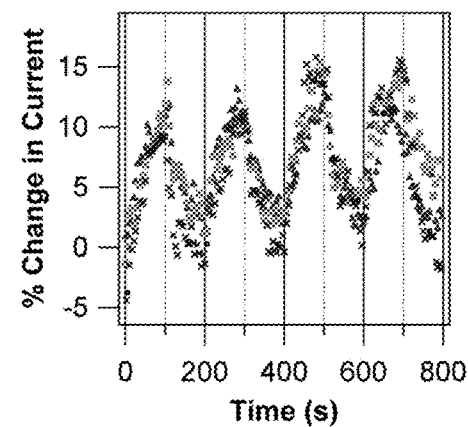
Figure 11C:
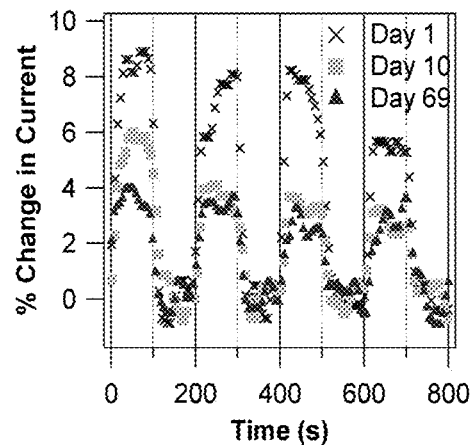

After fabrication, micelle devices remained active for ~5 days when stored in a humid environment. Devices then became fully inactive and displayed no response to odorant vapors, as was typical of un-functionalized nanotubes (see Table 1, FIG. 13). Nanodisc-functionalized devices showed ~25% reduction in odorant response over the first several days, but at this point the devices stabilized and functioned as sensors with very long lifetimes. When stored in a humid environment, devices showed reproducible responses for longer than one month, with one device maintaining mOR-specific responses to odorants for ten weeks (FIG. 11c).

Figure 11D:
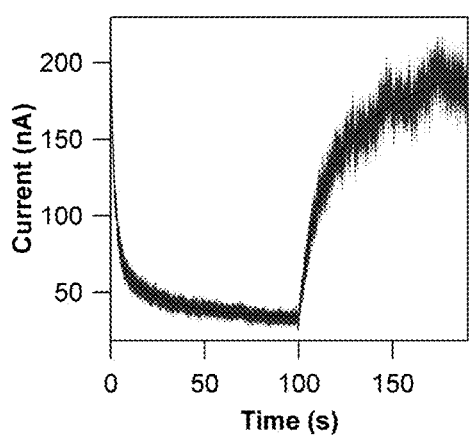
Figure 23A:
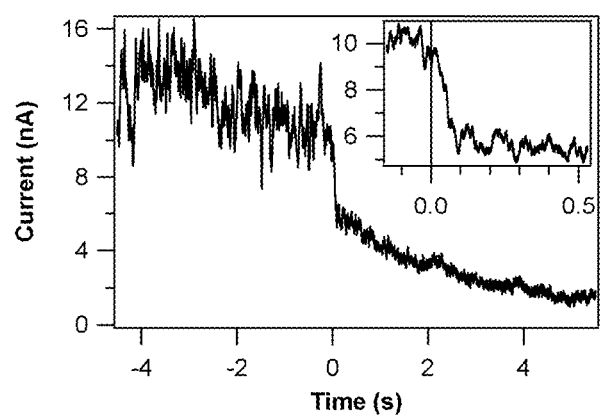
FIG. 23 presents a current response of a single-stranded DNA functionalized NT transistor to DMMP at 1500 ppm in the same chamber as was used for the mOR experiments. One typically observe a very rapid response in the first 0.1 seconds for NT devices functionalized with ssDNA, in contrast to the much slower response (~10-30 seconds) observed for the mOR-functionalized NT devices discussed in the main text.
Figure 23B:
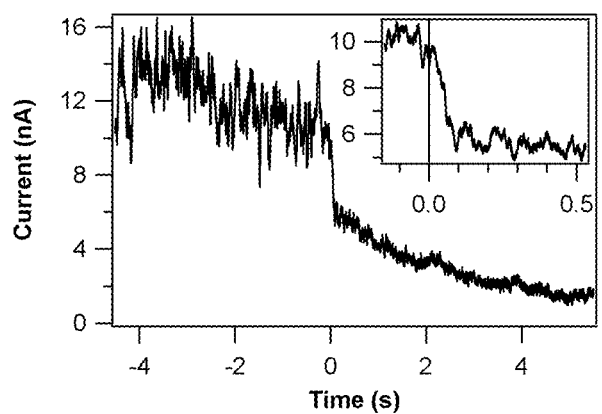

One may use a high-speed data acquisition system to investigate the shape and timing of device responses (FIG. 11D). It was found that the response and recovery data could be well fit with double exponential functions (blue lines in FIG. 11C), with significant response on timescales <10 sec. The observed timescales are intrinsic to the mOR-NT system, since control experiments indicated that the response time of the apparatus itself is <100 ms (FIG. 23). Response and recovery timescales show little variation with mOR identity or whether digitonin micelles or nanodiscs were used to solubilize the ORs. Response and recovery are significantly faster than found in heterologous measurements, where full response often takes tens to hundreds of seconds due to use of a signal transduction pathway to report receptor activation.

Measurements of responses of OR-functionalized devices such as those shown in FIG. 11 were made for a range of odorants and odorant concentrations. FIG. 12A shows the concentration dependence of the response of NT devices functionalized with mOR203-1 in digitonin micelles to several odorants, while FIG. 12B provides representative examples of how device responses varied with concentration, odorant, and mOR identity. To account for different vapor pressures of the odorants, concentrations are quantified as a fraction of the saturated vapor. FIG. 12A shows substantial agreement between the NT device measurements and the HEK data for this mOR, for example, the strong response to 2-heptanone and lack of response to heptanal and acetophenone. Interestingly, the NT device shows nearly identical responses to the chemically similar odorants 2-heptanone and n-amyl acetate. The molecules differ only by a single oxygen atom in the functional group attached to a 5-carbon chain, and they are perceived as nearly identical by humans. In mice, these two chemicals produce identical neural excitations, and olfactory responses, although the interaction of n-amyl acetate with the particular mOR 203-1 has not been measured previously. In other cases, odorants with related molecular structures elicit very distinct responses. For example, the other three odorants in FIG. 12A share a carbon ring motif but the odorant responses differ substantially.

Figure 24A:
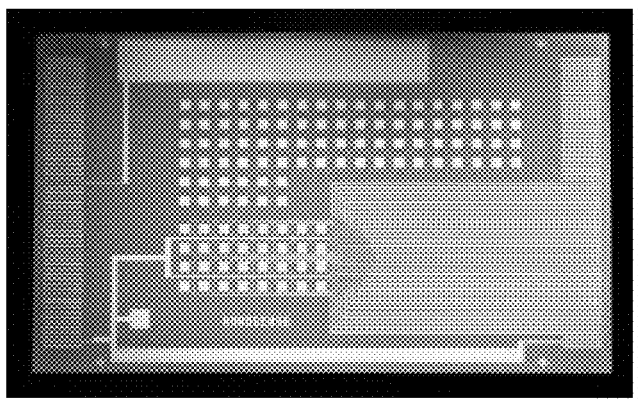
FIG. 24A provides an image of an array of mOR-functionalized NT devices used to establish the potential for large-scale production.
Figure 24B:
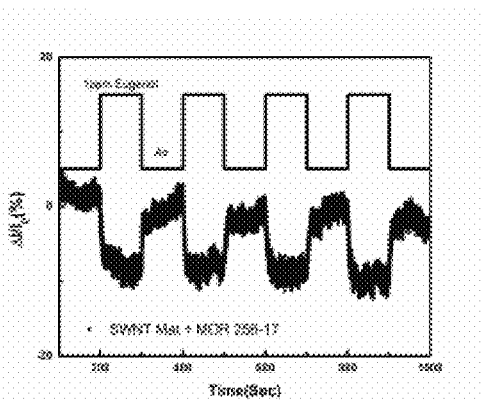
FIG. 24B provides in illustration of the response of one such device upon exposure to eugenol vapor at a concentration of 1 ppm. Sensing data are % change from background current.

Of the eight odorants tested, 2,4-dinitrotoluene is the only one not found in nature. It also produces a response at the lowest concentrations, ~7 ppb, in the range of a "moderately potent" detection threshold for an OR. It is not known whether mice can detect dinitrotoluenes, but there is strong evidence suggesting that they can be sensed by bomb-detecting dogs and rats. Mammalian olfactory systems have the ability to detect and categorize new odorants, even those not present during the evolutionary history of the organism, or the history of biological olfactory systems in general. This feature is beyond the capability of man-made chemical sensor systems. These results suggest that the capacity of mORs to bind to non-biological odorants is preserved when integrated with NT devices, maintaining the mOR's ability to adapt to new analytes. This system thus may be used in chemical sensor arrays that would have the flexibility of the biological sense of smell; fabrication of such arrays using existing lithography and liquid spotting methods has already been demonstrated (FIG. 24).

The data indicate that mOR-NT devices have characteristics that are typical of the function of ORs in vivo, such as the need for a humid environment, the relatively short lifetime of the devices, and the odorant response timing. The data summarized in Table I indicate that mOR-NT device responses to odorants show broad agreement with mOR odorant responses found using heterologous techniques for 2 of the 3 mORs tested, with only mOR 256-17 showing significant disagreement. Neither the NT nor heterologous systems duplicate the in vivo OR response exactly, but areas of agreement between these two test systems strengthen the interpretation of select sensitivities as present in the natural host.

For each type of experiment (*Xenopus* oocyte, HEK, and NT device), data are summarized in terms of relative sensing response. Blue indicates little or no response, red indicates a clear, strong response and purple indicates a moderate response. White boxes represent biological data that are not available. HEK data are from Ref 17. mOR-functionalized NT devices respond to odorants that elicit no response from bare NT devices or devices functionalized with empty micelles. Odorant sensitivities of mOR-functionalized NT devices vary with OR identity and are very similar to those seen in *Xenopus* and HEK experiments.

For mOR 174-9 and mOR 203-1, disagreements consist of a strong response by the NT device and a weak or no response in the heterologous system. Since the NT device response reflects all molecules that bind near it, this could reflect odorant binding to the mOR that elicits no cellular response (e.g., an antagonist) or possibly odorant binding to the NT itself or the digitonin micelle (or nanodisc) that encapsulates the mOR instead of the mOR itself. To exclude the latter possibilities, control experiments were conducted on bare NT transistors and on devices treated with Ni-NTA and empty digitonin micelles (i.e., no mOR). These results are included in Table I. No significant response to any of the tested odorants was observed, with the exception of cyclohexanone, where a small response was observed. One may infer from this that observed device responses reflect NT transistor readout of the binding affinity of the attached mORs, with the possible exception of cyclohexanone. This reasoning informs the interpretation of the data for mOR256-17, where there are several disagreements between the NT and heterologous data. This mOR shows the broadest set of chemical responses in the heterologous system. The synthetic membrane environments that used to house the OR may lead to subtle perturbations to the mOR structure, thereby shuffling the multiple affinities that characterize mOR256-17.

In conclusion, provided are purification, solubilization, and bio-functionalization schemes that enable control of the bio-nano interface between olfactory receptor (membrane) proteins and carbon nanotubes. Vapor response measurements demonstrate that ORs with known odorant sensing properties can be coupled to an electronic device and transfer many of those sensing properties to the device. Future work exploring additional ORs and other types of GPCRs could help to understand differences between protein-nanotube measurements, heterologous measurements and in vivo measurements. This opens up a very large domain of intra- and intercellular communication to electronic eaves-dropping and could serve as a powerful tool for molecular and cell biology research.

Materials and Methods—Additional

1. Electrophysiological Characterization of Mouse Olfactory Receptors (mORs) Expressed in *Xenopus* Oocytes Reference is made to mORs using the nomenclature of Zhang and Firestein. Receptor coding regions were cloned into the pCI expression vector (Promega) containing an N-terminal extension consisting of the N-terminal 20 amino acid residues of human rhodopsin. Receptors were coexpressed with human $Ga_{olf}$ and the human cystic fibrosis transmembrane regulator (CFTR), serving as a reporter channel.

Oocytes were surgically removed from mature *Xenopus laevis* frogs (Nasco). Follicle cells were removed by treatment with Collagenase B (Boehringer Mannhem) for 2 hours at room temperature. Oocytes were injected with cRNA in 23 nl of water. cRNA quantities injected per oocyte: mORs, 25 ng; $Ga_{olf}$, 10 ng, CFTR, 1 ng. Oocytes were incubated at 18° C. in Barth's saline (in mM: 88 NaCl, 1 KCl, 2.4 $NaHCO_3$, 0.3 $CaNO_3$, 0.41 $CaCl_2$, 0.82 $MgSO_4$, 15 HEPES, pH 7.5 and 12 µg/ml tetracycline) for 2-4 days prior to electrophysiological recording.

Odorant induced $Cl^-$ currents, resulting from cAMP mediated activation of the co-expressed CFTR reporter channel, were measured 2-4 days after cRNA injection using two-electrode voltage clamp in an automated parallel electrophysiology system (OpusExpress 6000A, Molecular Devices). Oocytes were perfused with ND96 (96 mM NaCl, 2 mM KCl, 1 mM $CaCl_2$, 1 mM $MgCl_2$, 5 mM HEPES, pH 7.5). Micropipettes were filled with 3M KCl and had resistances of 0.2-2.0 MQ. The holding potential was −70 mV. Current responses, filtered (4-pole, Bessel, low pass) at 20 Hz (−3 db) and sampled at 100 Hz, were captured and stored using OpusXpress 1.1 software (Molecular Devices). Analysis was done using Clampfit 9.1 software (Molecular Devices).

Electrophysiological results for mOR256-17 are at some variance with published reports that mOR256-17 responds to cyclohexanone, but not to heptanal or 2-heptanone.

2. Mouse Olfactory Receptor Expression in SF9 Cells a) mOR 174-9 and mOR 203-1

Recombinant mouse olfactory receptors (mOR) 174-9 and 203-1 were expressed in an Sf9 insect cell system using the BaculoDirect Expression System (Invitrogen). The entry clones for mOR 174-9 (Olfr73; BC141607) and 203-1 (Olfr992; BC141642) were from Invitrogen. The DNA sequence of each receptor was verified using primer pairs specific to each receptor. The DNA sequences of both mOR 174-9 and mOR 203-1 clones were verified using GW1 forward primer (GTTGCAACAAATTGATGAGCAATGC (SEQ ID NO: 1)) and GW2 reverse primer (GTTG-CAACAAATTGATGAGCAATTA (SEQ ID NO: 2)).

The entry clones were used to create an expression clone for each mOR through Linear Recombination (LR) reaction using BaculoDirect Linear DNA with an N-terminal His tag. Two recombinant expression clones were created: mOR 174-9 with N-terminal His tag, and mOR 203-1 with N-terminal His tag. All expression clones were used individually to transfect Sf9 insect cells. Six days after transfection, the cells demonstrated signs of infectivity. The viral stock was collected and was labeled P1 viral stock. The P1 viral stock was stored at ~80° C. in the dark with 10% fetal bovine serum (FBS) to protect the recombinant virus from proteases. Second and third rounds of viral amplification were performed and labeled P2 and P3 viral stocks, respectively. An aliquot of P3 viral stock was collected and used to isolate and purify the viral DNA for PCR to check the orientation of the mOR DNA fragment after transfection and expression.

The viral titer of all P3 viral stocks was determined following the protocol on the BacPAK™ Baculovirus Rapid Titer Kit (Clontech). Once the viral titer was known, Baculovirus Infected Insect Cell (BIIC) stock was prepared for each recombinant mOR. BIIC stock was found to be more stable than the viral stock. BIIC stock with multiplicity of infection (MOI) of 3 was prepared based on existing methodology. Sf9 cell cultures were infected with BIIC stock to express the recombinant mORs. The expression of all recombinant mORs was monitored by determining the % viability, total cell density and viable cell density during the infection process. A decrease in % viability and increase in both the cell diameter and viral titer can be observed during infection. While still in their log growth phase state, the cells were harvested, as the % viability of the Sf9 culture reached 70-80%. Cells were harvested by centrifugation (1,000×g, 10 min, 4° C.).

b) mOR 256-17 moR256-17 clone was placed in frame into pFastBac HT (Invitrogen) between EcoRI and NotI using common procedures for SF9 insect cells. Colonies were screened by pcr. Virus was generated using the Bac-to-Bac system (Invitrogen) according to the manufacturer's instructions. Virus was quantified by plaque assay. For protein production cells were grown in shaker flasks at 125 rpm at 27° C. either in Grace's supplemented medium with 10% FBS or SF900II medium with 2% FBS. Media also contained 0.25 mg/liter amphotericin B (Sigma A9528), 20 mg/liter gentamicin (Gibco 15750-060), and 0.1% Pluronic F-68 (Sigma P5556). Cells were infected at a multiplicity of infection of one at a cell density of 1 to $2 \times 10^6$ cells/mL. Cells were harvested 48 hours post infection, weighed, frozen in liquid nitrogen and stored at −80° C. Expression was confirmed by western blot using antipentahistidine ("pentahistidine" disclosed as SEQ ID NO: 3) primary antibody (Qiagen).

3. Purification of mORs for Incorporation into Digitonin Micelles a) Preparation of the Crude Plasma Membrane Fraction (CMF)

Cell pellets were washed initially by resuspending in a concentration of phosphate buffered saline (PBS) equivalent to the osmolality of the cell growth media and centrifuged (1000×g, 10 min, 4° C.). The pellets were resuspended in a lysis buffer consisting of 20 mM Tris-HCl (pH 8.0) 1 mM EDTA, 1 mM EGTA, 0.4% (v/v) ethanol, 0.1 mM (phenylmethanesulfonylfluoride (PMSF), and protease inhibitor cocktail designed for Sf9 cells (Sigma) and homogenized with a Dounce homogenizer (pestle A, 0.0030-0.0060 in.). In some cases, such as when there was a large amount of nuclei present in the homogenate (as evident from the presence of a clear jelly-like substance), the homogenized cell suspension was centrifuged (300×g, 10 min, 4° C.) to remove the more dense nuclei and unbroken cells. The homogenate, or supernatant in the case of the latter, was then centrifuged (40,000×g, 20 min, 4° C.) and the supernatant discarded. The pellets were resuspended in a solution of 20 mM Tris-HCl (pH 8.0), 3 mM $MgCl_2$, 0.5 mM $CaCl_2$, and 10 g/mL deoxyribonuclease (DNase)-I, and centrifuged (40,000×g, 20 min, 4° C.). The supernatant was discarded, and the pellet was resuspended in approximately 400 µL of 20 mM Tris-HCl (pH 8.0), 3 mM $MgCl_2$, 0.5 mM $CaCl_2$, and 10 µg/mL deoxyribonuclease (DNase)-I per 30 mL of cells harvested (ca. 0.75 mg total protein/mL cells harvested), using a 5 mL Wheaton homogenizer. Resuspended pellets were then aliquoted into Eppendorf tubes, flash frozen in liquid nitrogen, and stored at −80° C.

b) mOR Purification Using Nickel-Magnetic Beads

A 400 µL aliquot of CMF was solubilized in a solution such that its final composition was 6.76 mM Digitonin, 19 mM $NaH_2PO_4$, 115 mM NaCl, 12 mM Tris, 2 mM $MgCl_2$, 0.3 mM $CaCl_2$, and 6.2 µg/mL DNase-I. Solubilization of the CMF was achieved via agitation on a benchtop vertical rotator for 1 h, or via sonication with a microtip (Misonix Ultrasonic Liquid Processor). PureProteome™ Nickel-magnetic beads (Millipore) were added to the solubilized CMF in a volume of 50 mM $NaH_2PO_4$, 300 mM NaCl, pH 8.0, such that the final concentration of digitonin was 4.88 mM. The Ni-magnetic beads were mixed with solubilized CMF for 1 h at 4° C. on a vertical rotator and isolated with a magnet. The His-tagged protein was eluted from the beads with approximately 1.25 mL of 4.88 mM digitonin prepared with 100 mM acetate buffer (pH 4.0), and the pH was adjusted to 8.0 using a micropH electrode. The pH adjustment typically required no more than 0.2 mL NaOH.

4. Purification of mORs for Incorporation into Nanodiscs

A cell pellet was thawed on ice. Cells were resuspended (2.5 mL per gram cells) in ice cold PBS (Biowhittaker, without magnesium or calcium) containing Roche complete protease inhibitors without EDTA and Sigma inhibitor cocktail (Sigma, P8849). Cells were sonicated on ice using a Branson 450 sonifier at power 5, 80% duty cycle using a microprobe tip with eight 15 second bursts, waiting 30 s between bursts. The sample was centrifuged at 40 k rpm in a Ti70 rotor at 4° C. for 30 minutes. Ice cold PBS containing protease inhibitors and 2% w/v Fos-choline 12 (Anatrace) was added to the pellet, 2.5 mL per gram of cell starting material, and the sample was agitated in a Falcon tube at 4° C. for 2.5 hours. The sample was then centrifuged as before and supernatant loaded onto a 5 mL nickel chelating FF cartridge (GE Healthcare) in a cold room. The cartridge was washed with three volumes of PBS containing 20 mM imidazole (pH 7.4) and 0.4% w/v Fos-choline 12. Protein was eluted with PBS containing 500 mM imidazole (pH 7.4) and 0.4% w/v Fos-choline 12. Protein containing fractions were pooled and protein content measured using Coomassie Plus reagent (Pierce) with bovine serum albumin as standard.

5. Assembly of mOR Nanodiscs

Nanodiscs were assembled essentially as described previously. Briefly, MSP1E3D1(−) without a polyhistidine tag was mixed with a 0.2 M POPC/0.4 M cholate mixture prepared as described at a ratio of 140 moles POPC to one MSP1E3D1. Fos-choline 12 was added to a final concentration of 0.4%. Olfactory receptor was added to the MSP lipid mixture at a ratio of one milligram crude OR per twenty milligrams MSP1E3D1 (MW 32700). Protease inhibitor was added (Roche complete without EDTA) and detergent was removed at 4° C. with overnight agitation in the presence of an equal volume of moist Amberlite XAD-2, prepared as described. After removal of beads the sample was filtered using a 0.22 µm syringe filter and stored at 4° C.

6. Carbon Nanotube Transistor Fabrication

Carbon nanotubes were grown on p++ doped silicon wafers (4-inch diameter) with 500 nm thermal oxide from Silicon Valley Microelectronics. Approximately 5 mL of 50 mg/L iron nitrate solution was spun onto wafers at 2000 RPM until dry to provide growth catalyst. Wafers were broken into halves and annealed at 910° C. for 15 minutes.

Growth was performed in a 50 mm tube furnace at 910° C. in a flow of 2500 standard cubic centimeters per minute (sccm) methane and 320 sccm hydrogen with 600 sccm Argon as carrier gas for 10 minutes. The furnace temperature was then decreased to 100° C. over approximately 2 hours in a flow of 320 sccm hydrogen with 600 sccm argon before samples were removed from the furnace.

Nanotube transistor fabrication was carried out using optical lithography. Polymethylglutarimide (PMGI) (Microchem SFS2) was spun on at 4000 RPM for 45 seconds and samples were baked at 150° C. for 5 minutes. Photoresist (Shipley 1813) was spun on at 5000 RPM for 45 seconds, and samples were baked at 115° C. for 1 minute. After an exposure of about 100 $mW/cm^2$, Microposit MF-319 was used to develop devices for around 1 minute.

5 nm chrome and 50 nm gold were deposited in a home-built thermal evaporator. Liftoff was done in an acetone bath, followed by a bath in Microposit Remover-PG to remove the PMGI, then multiple clean water baths.

The resulting devices have a 2 μm source-drain separation. Before electrical measurement, chips were baked at 250° C. in air for 30 minutes to remove any polymeric residue from fabrication.

Typical nanotubes are single walled, with diameter of 1.0-2.5 nm. Typical devices have 1 to 3 nanotubes bridging the gold electrodes. Electrical data, using the silicon wafer as a transistor back-gate, is gathered on all devices before chemical modification. Devices showing on/off ratios exceeding 1000 were selected for use in experiments.

7. Chemical (Ni-NTA) Modification of Carbon Nanotubes

Carbon nanotube transistors on silicon wafers were chemically functionalized using a procedure similar to that described previously. All solutions were prepared using deionized water with an electrical resistance of 18.2 MΩ-cm. All chemical modifications were performed on the chips in 50-mL polypropylene Falcon tubes. First, samples were placed in a solution of 10.76 mM 4-carboxybenzene diazonium tetrafluoroborate at 45° C. for 1 h, followed by washing with acetone, methanol, and water. The chips were then placed in a solution of 2 mM EDC, 5 mM Sulfo-NHS, prepared with activation buffer (0.1 M 2-(N-Morpholino) ethanesulfonic acid (MES) sodium salt, 0.5 M NaCl, pH adjusted to 6.0 with HCl) at room temperature for 15 minutes to activate the carboxylic acid of the 4-carboxybenzene covalently attached to the nanotubes. Immediately afterwards, the chips were briefly bathed in activation buffer and placed in a solution of 11.3 mM $N_a$, $N_a$-Bis(carboxymethyl)-L-lysine hydrate (NTA-$NH_2$) prepared with phosphate buffered saline (PBS; 0.1 M $NaH_2PO_4$, 0.15 M NaCl, pH adjusted to 7.35 with NaOH) for 2 h. Upon completion, the chips were washed with water and placed in a solution of 11.3 mM $NiCl_2$. After 1 h, the chips were removed from the $NiCl_2$ solution, washed with water, and stored in 25% (v/v) ethanol, at 4° C.

8. Attachment of mORs to Ni-NTA Modified Nanotubes

Figure 20A:
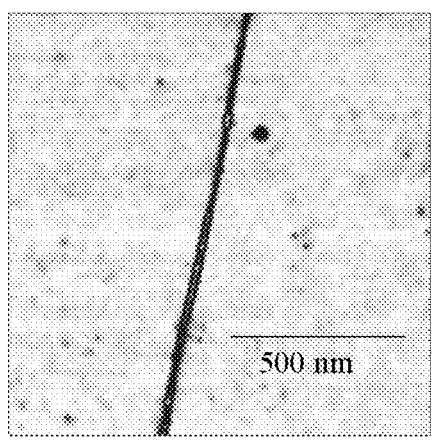
FIGS. 20A-20C present presents exemplary results—FIG. 20A provides an illustration of how water soluble, His-tagged proteins selectively bind to Ni-NTA functionalized carbon nanotubes. 20 nm height color scale.
Figure 20B:
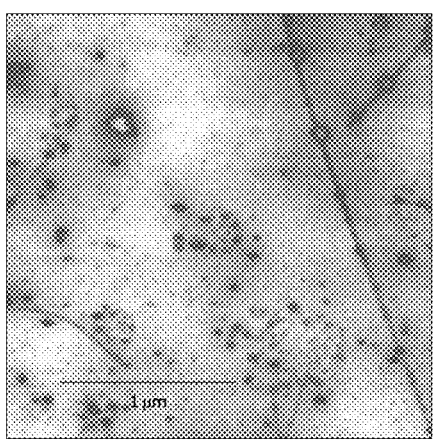
Figure 20C:
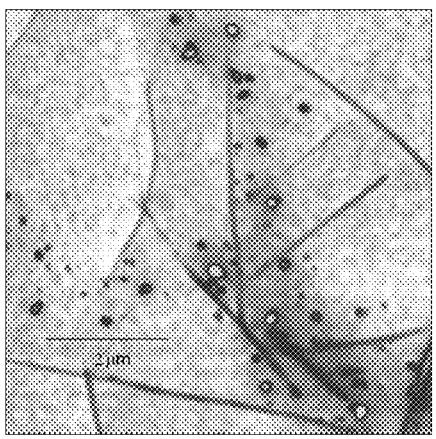
Figure 20D:
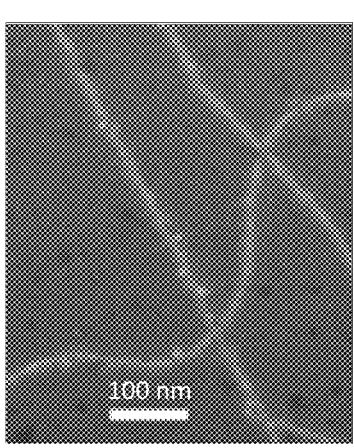
FIG. 20D provides a SEM image of His-tagged gold beads attached to Ni-NTA modified NTs. In each case, binding site densities of ~5-10 sites/µm of nanotube length were found.

Chips containing Ni-NTA modified nanotubes were removed from storage in ethanol, rinsed in water, and dried in a stream of high purity nitrogen or argon gas. A solution containing mORs in digitonin micelles or nanodiscs, prepared as described above, was deposited on the surface of the chips for 30 min, at room temperature. A large enough volume was deposited on the chips such that any volume change over the 30 min period due to evaporation was negligible. If the solution contained surfactant stabilized mORs, the chips were then rinsed with a 1 mM Digitonin solution. If the solution contained mORs in nanodiscs, the chips were rinsed with deionized water. All samples were dried in a stream of nitrogen or argon gas (with the exception of the sample shown in FIG. 20B, which was air dried to show the CNT-micelle interaction).

9. Apparatus for Measuring Response of NT Devices to Odorant Vapors

The procedure for these measurements is as described in Reference 35. The temperature, humidity, flow rate, and flow paths are controlled by a computer. The computer also communicates with and controls a Keithley 6485 Picoammeter that measures the current through the device. A digital acquisition card provides the 100 mV source-drain voltage and is connected to the analogue out of the Keithley 6485 to record high time resolution current data. The gate may be controlled by a Keithley 617 Programmable Electrometer.

MKS 1179A style mass flow controllers are used to create three flows of nitrogen. One steady flow of 1000 standard cubic centimeters per minute (sccm) is bubbled through water to provide a humidified stream of gas. The second "sample flow" is switched between a bubbler containing the odorant being tested and a bypass which is not exposed to any odorant. The last flow serves as a "background" to further dilute the sample flow. The "sample" and "background" flows are set so that they add up to a total flow of 1000 sccm. These three flows (humidity, sample and background) are combined and then fed into the sensing chamber. Throughout the measurement, the total flow rate, temperature and humidity do not change.

The devices sit in a stainless steel sensing chamber, with gold pogo pin contacts to the interrogated devices. The total volume of the sensing chamber is around 40 mL. Before the measurements, tubing, fittings, valves and the chamber are cleaned by rinsing with acetone, isopropyl alcohol and water, followed by baking for 1 hour at 150° C.

10. Chemical Analytes

All odorants used are liquids under ambient conditions except for 2,4-dinitrotoluene, which is a solid. Carrier gas was bubbled through liquid odorants and forced through a column containing compressed powder of 2,4-dinitrotoluene. Analytes were used in pure form.

All odorants were purchased from Alfa Aesar except for n-amyl acetate which was purchased from Sigma Aldrich.

Integration of modern nanoelectronic technology with the potent molecular machines of living organisms offers a pathway to advanced chemical sensing modalities and high throughput screening of ligand binding. While significant progress has been made along this path using soluble proteins and nucleic acids, integration of amphiphilic membrane proteins remains elusive despite their vital and varied functionality in living organisms. Presented here is a design and implementation of a practical nanoelectronic interface to G-protein coupled receptors (GPCRs), a large family of membrane proteins whose roles in the detection of molecules outside eukaryotic cells make them important pharmaceutical targets. Olfactory receptor proteins (ORs) are the most numerous class of GPCRs, representing transcription products of ~3% of the mammalian genome8. Here is presented a method to integrate ORs with carbon nanotube (NT) transistors. The resulting devices transduce signals associated with odorant binding to ORs in the gas phase under ambient conditions and show responses that are in excellent agreement with results from established assays for OR-ligand binding. The work represents significant progress on a path towards an electronic nose that can be directly compared to biological olfactory systems as well as a general method for the study of GPCR function in multiple domains using electronic readout.

Further data are provided in FIGS. 20-24, as described below.

1. Non-Specific Binding of Micelles to Functionalized NTs

Multiple AFM and SEM experiments were done to examine the binding of His-tagged proteins and micelles to functionalized and unfunctionalized nanotubes. The results are summarized in FIG. 20.

Control experiments were conducted using identical incubation and washing protocols to confirm that binding between mORs and the nanotube was controlled by the Ni-NTA:His-tag interaction. It was confirmed that empty digitonin micelles and empty nanodiscs have no affinity for Ni-NTA modified nanotubes. Experiments also exposed Ni-NTA functionalized devices to proteins without His-tags and confirmed that no bound proteins remain after the wash protocol. The proteins for these experiments were commercially obtained protein G; the mORs were not used since these were all His-tagged, and were not designed for His-tag removal. It is expected that the Ni-NTA:His-tag interaction will properly orient the protein on the nanotube, but this has not been verified through a structural measurement.

2. Western Blot Analysis after Receptor Purification on Ni Magnetic Beads.

Figure 21:
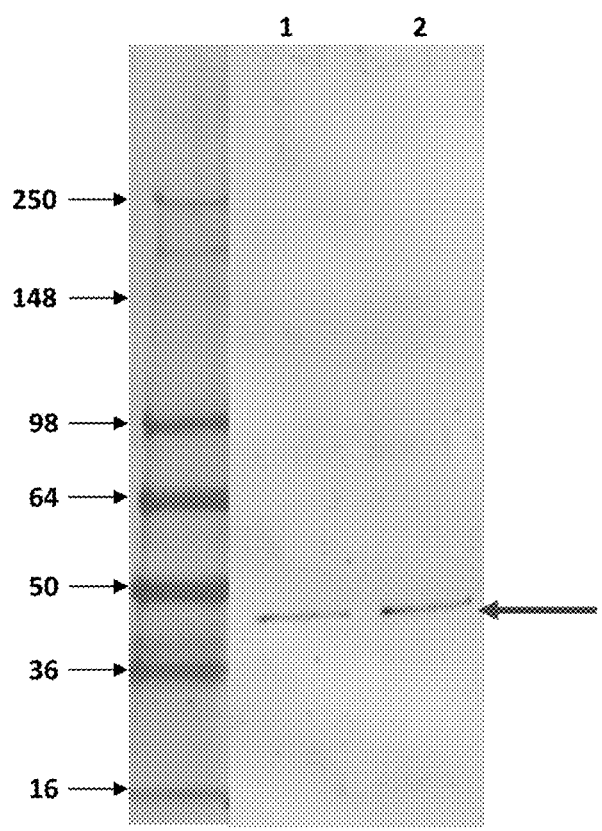
FIG. 21 presents Western blot analysis of purified mouse olfactory receptor (mOR) 174-9 (~40 kDa, red arrow). The receptor was purified using Ni magnetic beads and diluted 10 fold (line 1) and 25 fold (line 2). Western blot analysis was performed using Bio-Rad kit (chromogenic detection) probing the V5 epitope with anti-VS antibody. The V5 epitope is a sequence in the recombinant mOR located upstream of the natural mOR sequence and downstream of the His tag.
Figure 22A:
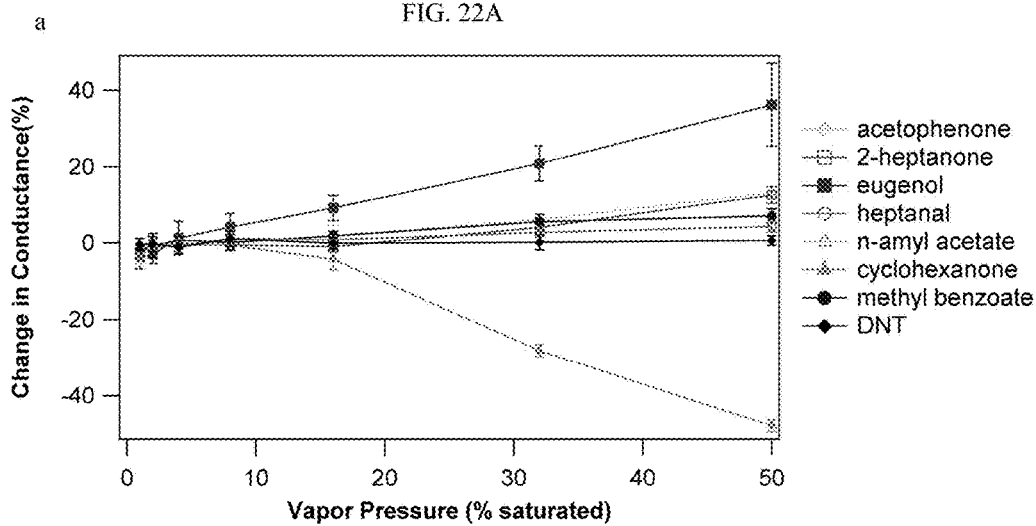
Figure 22B:
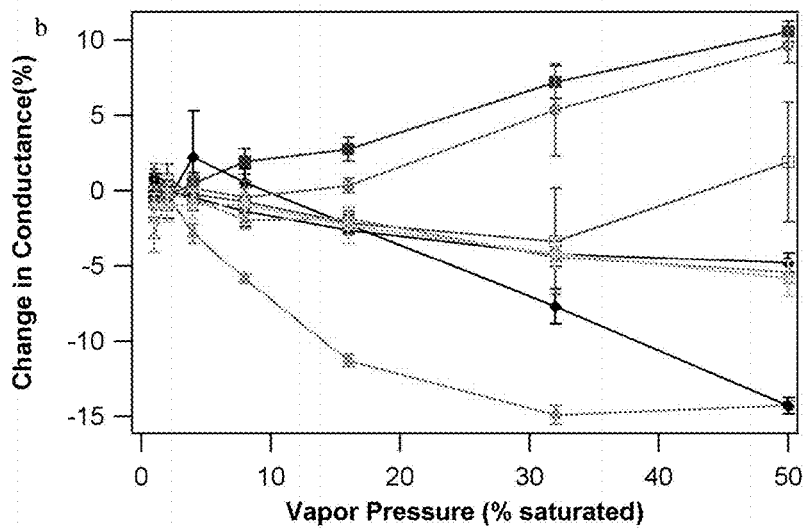
Figure 22E:
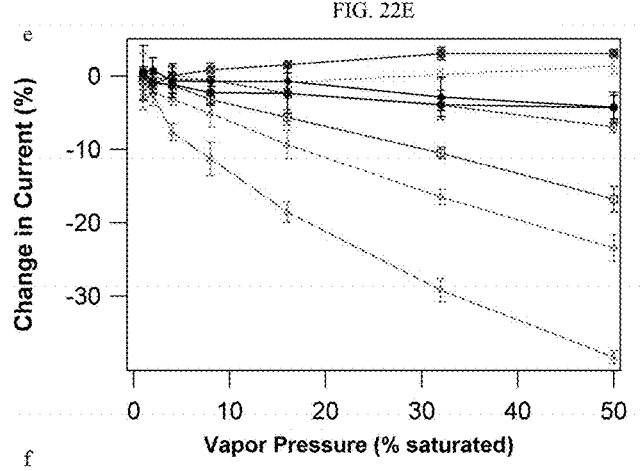
Figure 22F:
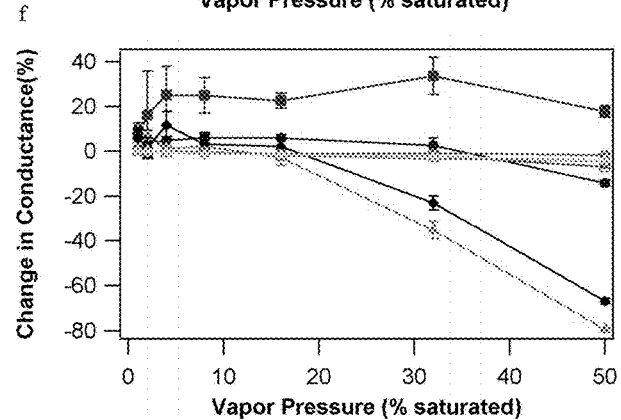

The correct molecular weight of each expressed mOR in the purified fractions was verified by Western blot analysis using antibody for His-tag or V5 epitope. FIG. 21 shows an example of Western blot for mOR 174-9.

3. Summary of NT Response Data

Figure 19:
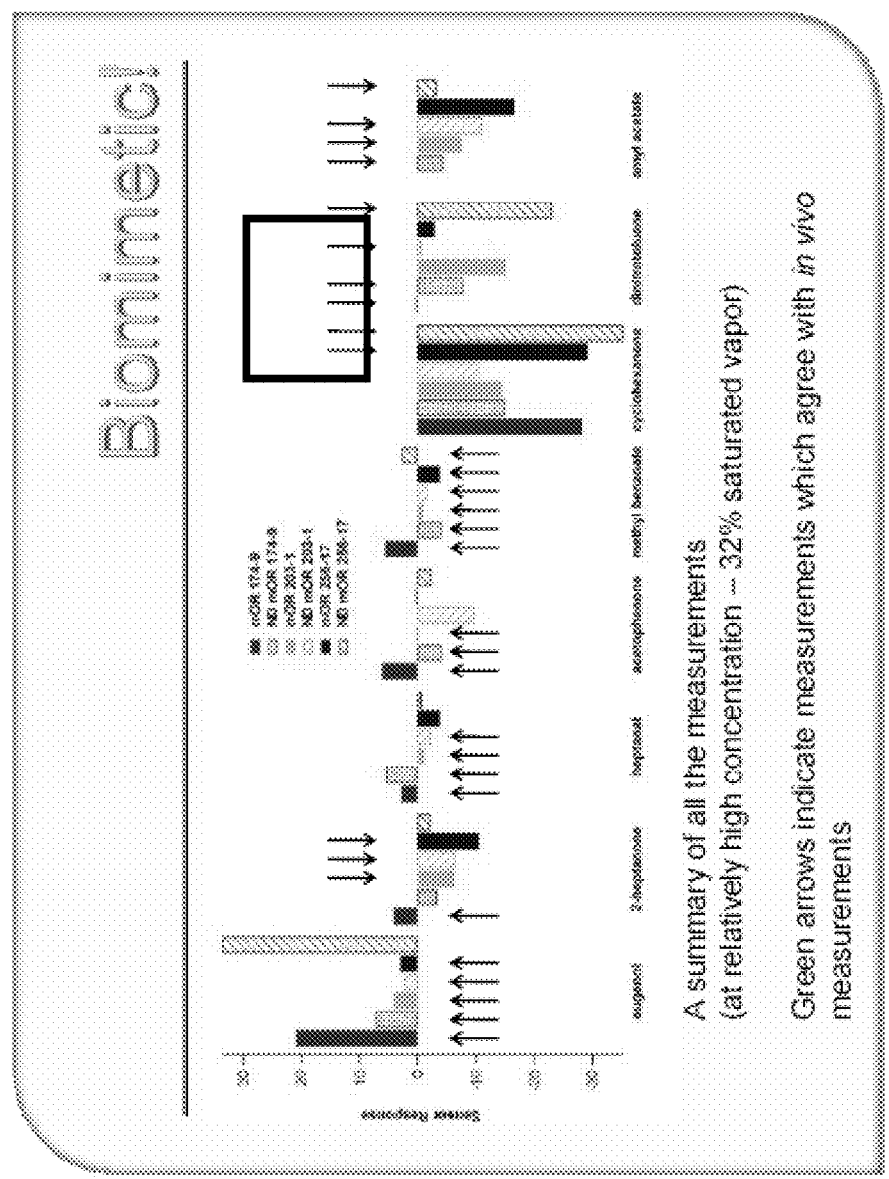
FIG. 19 illustrates exemplary data.

A summary of response data is shown in FIGS. 19 and 22.

4. Control Experiment to Determine Response Time of the Measurement Apparatus

The chamber used for measurements of the responses of NT Devices to odorant vapors is described in detail elsewhere herein. The speeds of gas introduction and flushing have been well characterized over several years of chemical sensing measurements on functionalized carbon nanotubes and with graphene. These earlier measurements demonstrate that the intrinsic response time of the measurement apparatus is below 100 ms.

Here is presented an example of a NT device functionalized with single stranded DNA (ssDNA) responds upon exposure to the odorant dimethylmethylphosphonate (DMMP). Other than the chemical treatment of the nanotube device and the odorant used, the measurement is performed identically to those presented in the main paper. A ~40% decrease in the device current occurs within 100 ms. FIG. 23 presents further detail.

5. Arrays of mOR-NT Devices

The chip in FIG. 24 is an array of 32 nanotube transistors functionalized with mOR-25-17 in digitonin micelles, sharing a common drain and back gate. The transistors consist of networks of nanotubes, unlike the few (1-3) tube devices discussed in the main paper. Flexible printed circuits (flex tabs) were used to interface the chip to a computer-controlled custom electronic system for signal conditioning and data acquisition. Fabrication was done on a 4" wafer using a commercially obtained 6" CVD furnace system to grow carbon nanotubes.

Device responses upon exposure to odorant vapors were collected as described in the main text, except that the total flow was 1000 sccm, and breathing grade air was used as the carrier gas for all flows. For the data shown below, the precise concentration of eugenol was verified using an FTIR spectrometer.

Additional background information may be found in the following. Each of these is incorporated herein by reference in its entirety.

1. Star, A., et al., *Electronic detection of specific protein binding using nanotube FET devices*. Nano Letters, 2003. 3(4): p. 459-463.
2. Zhang, Y. B., et al., *Functionalized carbon nanotubes for detecting viral proteins*. Nano Letters, 2007. 7(10): p. 3086-3091.
3. Zhou, X. J., et al., *Supported lipid bilayer/carbon nanotube hybrids*. Nature Nanotechnology, 2007. 2(3): p. 185-190.
4. Goldsmith, B. R., et al., *Conductance-controlled point functionalization of single-walled carbon nanotubes*. Science, 2007. 315(5808): p. 77-81.
5. Kojima, A., et al., *Protein sensor using carbon nanotube field effect transistor*. Japanese Journal of Applied Physics Part 1-Regular Papers Short Notes & Review Papers, 2005. 44(4A): p. 1596-1598.
6. Staii, C. and A. T. Johnson, *DNA-decorated carbon nanotubes for chemical sensing*. Nano Letters, 2005. 5(9): p. 1774-1778.
7. Zuniga, C., et al., *Nanoenabled microelectromechanical sensor for volatile organic chemical detection*. Applied Physics Letters, 2009. 94(22): p.
8. White, J., et al., *Solid-state, dye-labeled DNA detects volatile compounds in the vapor phase*. Plos Biology, 2008. 6(1): p. 30-36.
9. Kuang, Z. F., et al., *Biomimetic Chemosensor: Designing Peptide Recognition Elements for Surface Functionalization of Carbon Nanotube Field Effect Transistors*. Acs Nano, 2010. 4(1): p. 452-458.
10. McAlpine, M. C., et al., *Peptide-nanowire hybrid materials for selective sensing of small molecules*. Journal of the American Chemical Society, 2008. 130(29): p. 9583-9589.
11. Noy, A., A. B. Artyukhin, and N. Misra, *Bionanoelectronics with 1D materials*. Materials Today, 2009. 12(9): p. 22-31.
12. Akimov, V., et al., *Nanobiosensors based on individual olfactory receptors*. Analog Integrated Circuits and Signal Processing, 2008. 57(3): p. 197-203.
13. Bradley, K., et al., *Integration of cell membranes and nanotube transistors*. Nano Letters, 2005. 5(5): p. 841-845.
14. Yoon, H., et al., *Polypyrrole Nanotubes Conjugated with Human Olfactory Receptors: High-Performance Transducers for FET-Type Bioelectronic Noses*. Angewandte Chemie-International Edition, 2009. 48(15): p. 2755-2758.
15. Filmore, D., *It's a GPCR World*. Modem Drug Discovery, 2004. 7(11): p. 24-28.
16. Breer, H., *Olfactory receptors: molecular basis for recognition and discrimination of odors*. Analytical and Bioanalytical Chemistry, 2003. 377(3): p. 427-433.
17. Lundstrom, K. H. and M. L. Chiu, eds. *G Protein-Coupled Receptors in Drug Discovery*. Drug Discovery. 2006, CRC Press: Boca Raton.
18. Furton, K. G. and L. J. Myers, *The scientific foundation and efficacy of the use of canines as chemical detectors for explosives*. Talanta, 2001. 54(3): p. 487-500.
19. Christophe, C., et al., *Rats for demining: an overview of teh APOPO program*. Proceedings of the Eudem Conference on humanitarian landmine detection technologies, 2004.

20. Guo, X., et al., *Covalently bridging gaps in single-walled carbon nanotubes with conducting molecules.* Science, 2006. 311: p. 356-9.
21. Hulme, E. C. and N. J. M. Birdsall, *Receptor biochemistry: a practical approach.* 1990, Oxford; New York: IRL Press at Oxford University Press. xxi, 326.
22. Bayburt, T. H. and S. G. Sligar, *Self-assembly of single integral membrane proteins into soluble nanoscale phospholipid bilayers.* Protein Science, 2003. 12(11): p. 2476-2481.
23. Graff, R. A., T. M. Swanson, and M. S. Strano, *Synthesis of nickel-nitrilotriacetic acid coupled single-walled carbon nanotubes for directed self-assembly with polyhistidine-tagged proteins.* Chemistry of Materials, 2008. 20(5): p. 1824-1829.
24. Repicky, S. E. and C. W. Luetje, *Molecular receptive range variation among mouse odorant receptors for aliphatic carboxylic acids.* Journal of Neurochemistry, 2009. 109(1): p. 193-202.
25. Duchamp-Viret, P., M. A. Chaput, and A. Duchamp, *Odor response properties of rat olfactory receptor neurons.* Science, 1999. 284(5423): p. 2171-2174.
26. Khafizov, K., et al., *Ligand specificity of odorant receptors.* Journal of Molecular Modeling, 2007. 13(3): p. 401-409.
27. Raming, K., et al., *Cloning and Expression of Odorant Receptors.* Nature, 1993. 361(6410): p. 353-356.
28. Bayburt, T. H. and S. G. Sligar, *Membrane protein assembly into Nanodiscs.* Febs Letters, 2010. 584(9): p. 1721-1727.
29. Bahr, J. L., et al., *Functionalization of carbon nanotubes by electrochemical reduction of aryl diazonium salts: A bucky paper electrode.* Journal of the American Chemical Society, 2001. 123(27): p. 6536-6542.
30. Dan, Y. P., et al., *Intrinsic Response of Graphene Vapor Sensors.* Nano Letters, 2009. 9(4): p. 1472-1475.
31h. Heller, I., et al., *Identifying the mechanism of biosensing with carbon nanotube transistors.* Nano Letters, 2008. 8(2): p. 591-595.
32. Khalap, V. R., et al., *Hydrogen Sensing and Sensitivity of Palladium-Decorated Single-Walled Carbon Nanotubes with Defects.* Nano Letters, 2010. 10(3): p. 896-901.
33. Collins, P. G., et al., *Extreme oxygen sensitivity of electronic properties of carbon nanotubes.* Science, 2000. 287(5459): p. 1801-1804.
34. Sun, S. J., *Gas adsorption on a single walled carbon nanotube-model simulation.* Physics Letters A, 2008. 372 (19): p. 3493-3495.
35. Pengfei, Q. F., et al., *Toward large arrays of multiplex functionalized carbon nanotube sensors for highly sensitive and selective molecular detection.* Nano Letters, 2003. 3(3): p. 347-351.
36. Uchida, N. and Z. F. Mainen, *Speed and accuracy of olfactory discrimination in the rat.* Nature Neuroscience, 2003. 6(11): p. 1224-1229.
37. Azpiazu, I. and N. Gautam, *A fluorescence resonance energy transfer-based sensor indicates that receptor access to a G protein is unrestricted in a living mammalian cell.* Journal of Biological Chemistry, 2004. 279(26): p. 27709-27718.
38. Wilson, D. A., *Habituation of odor responses in the rat anterior piriform cortex.* Journal of Neurophysiology, 1998. 79(3): p. 1425-1440.
39. Schwende, F. J., D. Wiesler, and M. Novotny, *Volatile Compounds Associated with Estrus in Mouse Urine—Potential Pheromones.* Experientia, 1984. 40(2): p. 213-215.
40. Wise, P. M., M. J. Olsson, and W. S. Cain, *Quantification of odor quality.* Chemical Senses, 2000. 25(4): p. 429-443.
41. Xu, F. Q., et al., *Simultaneous activation of mouse main and accessory olfactory bulbs by odors or pheromones.* Journal of Comparative Neurology, 2005. 489(4): p. 491-500.
42. Albert, K. J., et al., *Cross-reactive chemical sensor arrays.* Chemical Reviews, 2000. 100(7): p. 2595-2626.
43. Lee, T. M. H., *Over-the-counter biosensors: Past, present, and future.* Sensors, 2008. 8(9): p. 5535-5559.
44. Ritchie, T. K., Grinkova, Y. V., Bayburt, T. H., Denisov, I. G., Zolnerciks, J. K., Atkins, W. M., and Sligar, S. G. (2009) "Reconstitution of Membrane Proteins in Phospholipid Bilayer Nanodiscs." Methods, Enzymol. 464, 211-231.
45. Nath, A., Atkins, W. M., and Sligar, S. G. (2007) "Applications of Phospholipid Bilayer Nanodiscs in the Study of Membranes and Membrane Proteins." Biochemistry 46, 2059-2069.

What is claimed is:

1. A device, comprising:
a semiconductor material comprising a carbon nanomaterial; and
a G-protein coupled receptor, the protein capable of changing conformation upon binding to a target,
the protein disposed in a support material capable of maintaining the protein in essentially its natural conformation, and
the protein being in electrical communication with the semiconductor material;
wherein a surface of the semiconductor material comprises a group linking the semiconductor to the protein.

2. The device of claim 1, wherein the semiconductor material comprises a carbon nanotube, graphene, silicon carbide, or any combination thereof.

3. The device of claim 2, wherein the carbon nanotube comprises a single-wall carbon nanotube.

4. The device of claim 2, wherein the carbon nanotube comprises a multi-wall carbon nanotube.

5. The device of claim 1, wherein the group includes a metal.

6. The device of claim 1, wherein the support material comprises a lipid, an amphiphile, a nanodisc, or any combination thereof.

7. The device of claim 6, wherein the amphiphile comprises digitonin.

8. The device of claim 1, wherein the support material comprises a micelle.

9. The device of claim 8, wherein the support material comprises a digitonin micelle.

10. The device of claim 9, wherein the receptor comprises an olfactory receptor.

11. The device of claim 1, wherein the protein comprises at least one histidine.

12. The device of claim 11, wherein the histidine links the protein to the semiconductor material.

13. The device of claim 1, further comprising at least one electrode in electronic communication with the semiconductor material.

14. The device of claim 1, wherein the carbon nanomaterial is graphene or a carbon nanotube.

15. The device of claim 1, wherein the carbon nanomaterial is graphene.

16. The device of claim 1, wherein the G-protein coupled receptor comprises an olfactory receptor.

17. The device of claim 1, wherein the G-protein coupled receptor comprises: adenosine, bombesin, bradykinin, endothelin, y-aminobutyric acid (GABA), hepatocyte growth factor (HGF), melanocortins, neuropeptide Y, opioid peptides, opsins, somatostatin, tachykinins, members of the vasoactive intestinal peptide family, vasopressin, dopamine, epinephrine, norepinephrine, histamine, glutamate, glucagon, acetylcholine, chemokines, prostaglandins, prostanoids, platelet-activating factor, leukotrienes, calcitonin, C5a anaphylatoxin, follicle-stimulating hormone (FSH), gonadotropin-releasing hormone (GnRH), neurokinin, thyrotropin-releasing hormone (TRH), or oxytocin.

18. A sensor system, comprising:
a G-protein coupled receptor in essentially its natural conformation,
the protein being in electronic communication with a semiconductor material comprising a carbon nanomaterial; and
a detector device capable of detecting changes in one or more electronic characteristics of the protein related to an interaction between the protein and an analyte;
wherein a surface of the semiconductor material comprises a group linking the semiconductor to the protein.

19. The sensor system of claim 18, wherein the protein is disposed in a lipid, an amphiphile, a nanodisc, or any combination thereof, so as to be maintained in essentially its natural conformation.

20. The sensor system of claim 18, wherein the electronic communication between the protein and the semiconductor material comprises a coordination, a covalent bond, an ionic bond, or any combination thereof.

21. The sensor system of claim 18, wherein the semiconductor comprises a carbon nanotube, graphene, silicon carbide, or any combination thereof.

22. The sensor system of claim 18, wherein the detector device comprises a current monitor.

* * * * *

UNITED STATES PATENT AND TRADEMARK OFFICE
CERTIFICATE OF CORRECTION

PATENT NO. : 9,612,240 B2
APPLICATION NO. : 13/807323
DATED : April 4, 2017
INVENTOR(S) : Johnson, Jr. et al.

Page 1 of 1

It is certified that error appears in the above-identified patent and that said Letters Patent is hereby corrected as shown below:

On the Title Page

Item (73) delete: "The Trustees Of The University Of Pennsylvania"
Insert: --The Trustees Of The University Of Pennsylvania And The Board
    Of Trustees Of The University Of Illinois--

Signed and Sealed this
Third Day of October, 2017

Joseph Matal
*Performing the Functions and Duties of the*
*Under Secretary of Commerce for Intellectual Property and*
*Director of the United States Patent and Trademark Office*

```
                         SEQUENCE LISTING

<160> NUMBER OF SEQ ID NOS: 3

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gttgcaacaa attgatgagc aatgc                                         25

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 2
gttgcaacaa attgatgagc aatta                                              25

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      5xHis tag

<400> SEQUENCE: 3

His His His His His
1               5
```